US012642292B2

(12) United States Patent
Jensen et al.

(10) Patent No.: US 12,642,292 B2
(45) Date of Patent: Jun. 2, 2026

(54) MULTI-COMPARTMENT ORAL POUCHED PRODUCT

(71) Applicant: NICOVENTURES TRADING LIMITED, London (GB)

(72) Inventors: Kasper H. Jensen, Hellerup (DK); Ronald Keith Hutchens, East Bend, NC (US); Alexandre Mendes Campos, Porto Alegre (BR); Christopher Keller, Collierville, TN (US); Travis O'Neal, Pinnacle, NC (US); Matthew D. Sain, Mocksville, NC (US); Darrell Vian, Winston-Salem, NC (US); Lorenzo Uberti, London (GB)

(73) Assignee: NICOVENTURES TRADING LIMITED, London (GB)

( * ) Notice: Subject to any disclaimer, the term of this patent is extended or adjusted under 35 U.S.C. 154(b) by 808 days.

(21) Appl. No.: 17/732,490

(22) Filed: Apr. 28, 2022

(65) Prior Publication Data

US 2022/0354155 A1 Nov. 10, 2022

Related U.S. Application Data

(60) Provisional application No. 63/182,381, filed on Apr. 30, 2021.

(51) Int. Cl.
*A24B 13/00* (2006.01)
*A24B 15/16* (2020.01)
(Continued)

(52) U.S. Cl.
CPC .............. *A24B 13/00* (2013.01); *A24B 15/16* (2013.01); *A61K 9/009* (2013.01); *B32B 5/022* (2013.01);
(Continued)

(58) Field of Classification Search
None
See application file for complete search history.

(56) References Cited

U.S. PATENT DOCUMENTS

| | | | | |
|---|---|---|---|---|
| 2,475,241 | A | 7/1949 | Hermanson | |
| 3,338,992 | A * | 8/1967 | George | D01D 5/08 264/479 |

(Continued)

FOREIGN PATENT DOCUMENTS

| | | | |
|---|---|---|---|
| GB | 2319265 | | 5/1998 |
| JP | 2010534475 | A | 11/2010 |

(Continued)

OTHER PUBLICATIONS

Kiekins et al., "Non-Wovens From Cotton Fibres for Absorbent Products Obtained by the Needle-Punching Process," AUTEX Research Journal, Dec. 2002, 2(4), 9 pp.

(Continued)

*Primary Examiner* — Manley L Cummins, IV
(74) *Attorney, Agent, or Firm* — WOMBLE BOND DICKINSON (US) LLP

(57) ABSTRACT

The disclosure provides compositions adapted for oral use and, in particular, multi-compartment oral pouched products including such compositions. Some aspects of the disclosure relate to oral pouched products including a composition adapted for oral use within a porous pouch. In particular, the porous pouch may include two or more compartments, each compartment having a content of the composition contained therein. The composition within each compartment can be different such that the composition within each compartment provides a different functional or sensory experience, such as through use of a different flavoring agent, a different active ingredient, or both a different flavoring agent and a different active ingredient.

19 Claims, 4 Drawing Sheets

(51) Int. Cl.

| | |
|---|---|
| ***A61K 9/00*** | (2006.01) |
| ***B32B 5/02*** | (2006.01) |
| ***B32B 5/26*** | (2006.01) |
| ***B32B 7/022*** | (2019.01) |

(52) U.S. Cl.

CPC ................ *B32B 5/024* (2013.01); *B32B 5/26* (2013.01); *B32B 7/022* (2019.01); *B32B 2250/20* (2013.01); *B32B 2262/02* (2013.01); *B32B 2262/0276* (2013.01); *B32B 2262/0284* (2013.01); *B32B 2262/04* (2013.01); *B32B 2262/062* (2013.01); *B32B 2262/065* (2013.01); *B32B 2262/08* (2013.01); *B32B 2307/7163* (2013.01); *B32B 2307/726* (2013.01); *B32B 2439/40* (2013.01)

(56) References Cited

U.S. PATENT DOCUMENTS

| | | | | |
|---|---|---|---|---|
| 3,341,394 | A | 9/1967 | Kinney | |
| 3,502,763 | A | 3/1970 | Hartmann | |
| 3,542,615 | A | 11/1970 | Dobo et al. | |
| 3,692,618 | A | 9/1972 | Dorschner et al. | |
| 3,734,812 | A | 5/1973 | Yazawa | |
| 3,802,817 | A | 4/1974 | Matsuki et al. | |
| 3,849,241 | A | 11/1974 | Buntin et al. | |
| 3,972,759 | A | 8/1976 | Buntin | |
| 4,340,563 | A | 7/1982 | Appel et al. | |
| 4,622,259 | A | 11/1986 | McAmish et al. | |
| 4,907,605 | A | 3/1990 | Ray et al. | |
| 5,167,244 | A | 12/1992 | Kjerstad | |
| 5,200,246 | A | 4/1993 | Sabee | |
| 5,334,446 | A | 8/1994 | Quantrille et al. | |
| 7,032,601 | B2 | 4/2006 | Atchley et al. | |
| 7,498,281 | B2 | 3/2009 | Iwasaki et al. | |
| 7,861,728 | B2 | 1/2011 | Holton, Jr. et al. | |
| 7,950,399 | B2 | 5/2011 | Winterson et al. | |
| 7,980,251 | B2 | 7/2011 | Winterson et al. | |
| 8,124,147 | B2 | 2/2012 | Cheng et al. | |
| 8,336,557 | B2 | 12/2012 | Kumar et al. | |
| 8,557,071 | B2 | 10/2013 | Weiler | |
| 8,627,828 | B2 | 1/2014 | Strickland et al. | |
| 8,747,562 | B2 | 6/2014 | Mishra et al. | |
| 8,833,378 | B2 | 9/2014 | Axelsson et al. | |
| 8,846,075 | B2 | 9/2014 | Jonsson et al. | |
| 8,863,755 | B2 | 10/2014 | Zhuang et al. | |
| 8,931,493 | B2 | 1/2015 | Sebastian et al. | |
| 8,978,661 | B2 | 3/2015 | Atchley et al. | |
| 8,992,974 | B2 | 3/2015 | McCarty | |
| 9,066,540 | B2 | 6/2015 | Atchley et al. | |
| 9,125,434 | B2 | 9/2015 | Fuisz | |
| 9,161,567 | B2 | 10/2015 | Shikata et al. | |
| 9,161,908 | B2 | 10/2015 | Nilsson | |
| 9,167,835 | B2 | 10/2015 | Sengupta et al. | |
| 9,185,931 | B2 | 11/2015 | Gao et al. | |
| 9,358,296 | B2 | 6/2016 | McCarty | |
| 9,402,414 | B2 | 8/2016 | Griscik et al. | |
| 9,402,809 | B2 | 8/2016 | Axelsson et al. | |
| 9,414,624 | B2 | 8/2016 | Carroll et al. | |
| 9,462,827 | B2 | 10/2016 | Carroll et al. | |
| 9,468,233 | B2 | 10/2016 | Macko et al. | |
| 9,521,864 | B2 | 12/2016 | Gao et al. | |
| 9,693,582 | B2 | 7/2017 | Carroll et al. | |
| 9,848,634 | B2 | 12/2017 | Fuisz | |
| 9,854,830 | B2 | 1/2018 | Gao et al. | |
| 9,854,831 | B2 | 1/2018 | Gao et al. | |
| 9,884,015 | B2 | 2/2018 | Gao et al. | |
| 9,925,145 | B2 | 3/2018 | Hübinette et al. | |
| 9,930,909 | B2 | 4/2018 | Gao et al. | |
| 9,986,756 | B2 | 6/2018 | Gao et al. | |
| 9,999,243 | B2 | 6/2018 | Gao et al. | |
| 10,105,320 | B2 | 10/2018 | Gao et al. | |
| 10,130,120 | B2 | 11/2018 | Mishra et al. | |
| 10,244,786 | B2 | 4/2019 | Gao et al. | |
| 10,258,076 | B2 | 4/2019 | Carroll et al. | |
| 10,315,889 | B2 | 6/2019 | Kreischer et al. | |
| 10,327,467 | B2 | 6/2019 | Carroll et al. | |
| 10,334,873 | B2 | 7/2019 | Mishra et al. | |
| 10,463,070 | B2 | 11/2019 | Carroll et al. | |
| 10,609,949 | B2 | 4/2020 | Hodin et al. | |
| 10,647,459 | B2 | 5/2020 | Persson | |
| 10,959,456 | B2 * | 3/2021 | Sebastian ............... | B65D 65/46 |
| 2004/0121689 | A1 | 6/2004 | Anderson et al. | |
| 2004/0166756 | A1 | 8/2004 | Kurihara et al. | |
| 2005/0061339 | A1 | 3/2005 | Hansson et al. | |
| 2007/0062549 | A1 | 3/2007 | Holton et al. | |
| 2007/0122526 | A1 * | 5/2007 | Sweeney ................. | A23L 27/20<br>426/77 |
| 2008/0029110 | A1 | 2/2008 | Dube et al. | |
| 2008/0085649 | A1 | 4/2008 | Salamero et al. | |
| 2008/0249492 | A1 | 10/2008 | Schmidt | |
| 2008/0317911 | A1 | 12/2008 | Schleef et al. | |
| 2009/0022917 | A1 * | 1/2009 | Gedevanishvili ...... | A24B 13/00<br>427/430.1 |
| 2009/0025739 | A1 * | 1/2009 | Brinkley .............. | A24B 15/183<br>131/352 |
| 2009/0133704 | A1 | 5/2009 | Strickland et al. | |
| 2010/0330236 | A1 | 12/2010 | Miyahara et al. | |
| 2011/0180087 | A1 | 7/2011 | Gee et al. | |
| 2011/0268809 | A1 | 11/2011 | Brinkley et al. | |
| 2011/0303232 | A1 | 12/2011 | Williams | |
| 2011/0303511 | A1 | 12/2011 | Brinkley et al. | |
| 2012/0051672 | A1 | 3/2012 | Foss et al. | |
| 2012/0055493 | A1 | 3/2012 | Novak, III et al. | |
| 2012/0237640 | A1 | 9/2012 | Buffet et al. | |
| 2013/0206150 | A1 | 8/2013 | Duggins et al. | |
| 2013/0251779 | A1 | 9/2013 | Svandal et al. | |
| 2013/0276801 | A1 | 10/2013 | Byrd et al. | |
| 2014/0026912 | A1 | 1/2014 | Rushforth et al. | |
| 2014/0083438 | A1 | 3/2014 | Sebastian et al. | |
| 2014/0130813 | A1 * | 5/2014 | Strehle ................... | A24B 13/00<br>131/359 |
| 2014/0141677 | A1 | 5/2014 | Tai et al. | |
| 2014/0255452 | A1 | 9/2014 | Reddick et al. | |
| 2015/0096573 | A1 | 4/2015 | Gao et al. | |
| 2015/0096574 | A1 | 4/2015 | Gao et al. | |
| 2015/0096576 | A1 | 4/2015 | Gao et al. | |
| 2016/0000140 | A1 | 1/2016 | Sebastian et al. | |
| 2016/0073689 | A1 | 3/2016 | Sebastian et al. | |
| 2016/0157515 | A1 | 6/2016 | Chapman et al. | |
| 2016/0192703 | A1 | 7/2016 | Sebastian et al. | |
| 2016/0208440 | A1 | 7/2016 | Byrd et al. | |
| 2017/0188622 | A1 | 7/2017 | Wilson, V | |
| 2017/0280764 | A1 | 10/2017 | Sahlén et al. | |
| 2017/0318858 | A1 | 11/2017 | Hodin et al. | |
| 2018/0140007 | A1 | 5/2018 | Aspgren et al. | |
| 2018/0153211 | A1 | 6/2018 | Persson | |
| 2018/0255826 | A1 | 9/2018 | Persson et al. | |
| 2019/0255035 | A1 | 8/2019 | Bruun | |
| 2019/0291900 | A1 | 9/2019 | Persson et al. | |
| 2020/0037638 | A1 | 2/2020 | Faraci et al. | |
| 2020/0128870 | A1 | 4/2020 | Hassler et al. | |
| 2020/0275689 | A1 | 9/2020 | Lewerenz | |
| 2020/0297026 | A1 | 9/2020 | Kannisto et al. | |
| 2020/0383372 | A1 | 12/2020 | Stahl et al. | |
| 2020/0383373 | A1 | 12/2020 | Stahl et al. | |
| 2021/0206554 | A1 * | 7/2021 | Holton, Jr. ........... | A24B 15/308 |
| 2021/0235752 | A1 | 8/2021 | Fransén et al. | |

FOREIGN PATENT DOCUMENTS

| | | | |
|---|---|---|---|
| WO | WO 2007/037962 | 4/2007 | |
| WO | 2009/015142 A2 | 1/2009 | |
| WO | WO 2019/036243 | 2/2019 | |
| WO | WO-2020016432 A1 * | 1/2020 | ............. A24B 13/02 |

OTHER PUBLICATIONS

Patel et al., "Needle Punching Technology," Department of Textile Engineering, The Maharaha Sayajirao University of Baroda, Vadodara, Feb. 2010, 9 pp.

(56) References Cited

OTHER PUBLICATIONS

Pinnau et al., "Formation and Modification of Polymeric Membranes: Overview," Membrane Formation and Modification, ACS Symposium Series, American Chemical Society: Washington, DC, 1999, 22 pp.

* cited by examiner

MULTI-COMPARTMENT ORAL POUCHED PRODUCT

CROSS-REFERENCE TO RELATED APPLICATIONS

The present application is claims the benefit of and priority to U.S. Provisional Patent Application No. 63/182,381, filed Apr. 30, 2021, the disclosure of which is incorporated herein by reference in its entirety.

FIELD OF THE DISCLOSURE

The present disclosure relates to flavored products intended for human use. The products are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference. Oral products in similar formats and which are free of tobacco have also been proposed.

It would be desirable to provide products configured for oral use which may deliver active ingredients to the consumer in an enjoyable form.

BRIEF SUMMARY

The present disclosure generally provides oral products, including, but not limited to, all-white snus portions. The products may be configured to impart a taste when used orally and, additionally or alternatively, may deliver active ingredients to a consumer, such as nicotine. The products and methods of the present disclosure in particular relate to oral pouched products having multiple compartments therein (e.g., such as two, three, four, or more compartments) which each individually contain a composition intended for oral use.

Some aspects of the present disclosure provide for oral pouched products having an outer water-permeable pouch divided into two or more compartments. In some embodiments, the two or more compartments may include a first compartment and a second compartment. For example, in certain embodiments, each of said first and second compartments may contain a composition comprising a water-soluble component capable of release through the outer water-permeable pouch. Such compositions typically include an active ingredient (e.g., nicotine) and/or a flavoring agent as the water soluble component capable of release through the outer water-permeable pouch. In certain embodiments, the first compartment and the second compartment may be separated by a wall structure. For example, the wall structure may provide either a nonporous barrier that prevents inter-compartment transfer of the composition contained within each compartment or a porous barrier that allows inter-compartment transfer of the composition contained within each compartment.

The configuration and/or form of the wall structure may vary as desired. In some embodiments, for example, the wall structure is in the form of a fully or partially welded seam in the outer water-permeable pouch. In certain embodiments, for example when the wall structure allows inter-compartment transfer of the composition, the wall structure may be in the form of a perforated seam. In addition, the configuration and/or arrangement of the two or more compartments within the outer water-permeable pouch may vary as desired. For example, in some embodiments, the first compartment and the second compartment are arranged in a side-by-side configuration. In other embodiments, the first compartment and the second compartment are arranged in a layered configuration. In such embodiments, the wall structure may be a water-permeable barrier separating the first compartment and the second compartment. In still other embodiments, the oral pouched product may include a sealed outer perimeter adjacent to the first compartment, wherein at least a portion of the wall structure is in spaced relation to the sealed outer perimeter. In such embodiments, the wall structure has a first end and a second end, and the first end and the second end are proximal to the sealed outer perimeter. In certain embodiments, the wall structure forms a lateral perimeter surrounding a periphery of the second compartment such that the entirety of the wall structure is in spaced relation to the sealed outer perimeter. In such embodiments, the second compartment is contained entirely within the first compartment such that the first compartment surrounds the second compartment.

Typically, the composition within each of the first and second compartments can be the same or different. Advantageously, the multi-compartment oral products provided herein allow for different compositions to be positioned in each individual compartment. By positioning a different composition within each of the first and second compartments, the composition within each compartment can, in some embodiments, provide a different functional or sensory experience. In some embodiments, the composition within the first compartment and the composition within the second compartment comprise a different flavoring agent, a different active ingredient, or both a different flavoring agent and a different active ingredient. In some embodiments, the composition in the first compartment and the composition in the second compartment each comprise an active ingredient selected from the group consisting of a nicotine component, botanicals, nutraceuticals, stimulants, amino acids, vitamins, cannabinoids, cannabimimetics, terpenes, and combinations thereof. In some embodiments, the composition in the first compartment and the composition in the second compartment each comprise one or more additives selected from the group consisting of a flavoring agent, a salt, a sweetener, a binding agent, water, a humectant, a buffering agent and/or a pH adjuster, a tobacco material, and combinations thereof. In some embodiments, the oral products described herein may be substantially free of a tobacco material.

Typically, outer water-permeable pouch materials as described herein may comprise a fleece material and/or a water-dispersible film material. In some embodiments, fleece materials as described herein may include fibers selected from the group consisting of conventional cellulosic fibers, cotton fibers, wool fibers, polymer/synthetic-type fibers, and combinations thereof. In some embodiments, water-dispersible film materials as described herein may include a film forming material selected from the group consisting of film-forming polysaccharides, starches, modified starches, celluloses, modified celluloses, pullulan, pectin, alginate, gums, and combinations thereof. In some embodiments, the first compartment and the second compartment are separated by a fully or partially welded seam in the outer water-permeable pouch material. In certain embodiments, the outer water-permeable pouch may comprise a first layer of fleece material and a second layer of fleece material. In some such embodiments, for example, the outer water-permeable pouch may further comprise at least one intermediate layer of fleece material separating the first compartment and the second compartment. In such embodiments, the first layer of fleece material, the second layer of fleece material, and the intermediate layer of fleece material are welded together along a perimeter thereof to form a sealed outer perimeter of the oral pouched product.

In certain embodiments, the first layer of fleece material and the second layer of fleece material may be the same or different. In some embodiments, for example, the first layer of fleece material and the second layer of fleece material may be different such that the first and second layers of fleece material provide a different functional or sensory experience. For example, in one or more embodiments, the first layer of fleece material may include a different flavoring agent, a different active ingredient, or both a different flavoring agent and a different active ingredient when compared to the second layer of fleece material. In other embodiments, the first layer of fleece material may exhibit one or more of a different porosity, a different permeability, and a different texture when compared to the second layer of fleece material.

The disclosure includes, without limitations, the following embodiments.

Embodiment 1: An oral pouched product, comprising an outer water-permeable pouch divided into two or more compartments including a first compartment and a second compartment, each of said first and second compartments containing a composition comprising a water-soluble component capable of release through the outer water-permeable pouch.

Embodiment 2: The oral pouched product of embodiment 1, wherein the first compartment and the second compartment are separated by a wall structure, the wall structure providing either a nonporous barrier that prevents inter-compartment transfer of the composition contained within each compartment or a porous barrier that allows inter-compartment transfer of the composition contained within each compartment.

Embodiment 3: The oral pouched product according to any of embodiments 1-2, wherein the wall structure is in the form of a fully or partially welded seam.

Embodiment 4: The oral pouched product according to any of embodiments 1-3, wherein the partially welded seam is in the form of a perforated seam.

Embodiment 5: The oral pouched product according to any of embodiments 1-4, wherein the first compartment and the second compartment are arranged in a side-by-side configuration.

Embodiment 6: The oral pouched product according to any of embodiments 1-5, wherein the wall structure is a water-permeable barrier contained within the outer water-permeable pouch.

Embodiment 7: The oral pouched product of embodiment 6, wherein the first compartment and the second compartment are arranged in a layered configuration separated by the water permeable barrier.

Embodiment 8: The oral pouched product according to any of embodiments 1-7, further comprising a sealed outer perimeter adjacent to the first compartment, wherein at least a portion of the wall structure is in spaced relation to the sealed outer perimeter.

Embodiment 9: The oral pouched product according to any of embodiments 1-8, wherein the wall structure has a first end and a second end, and the first end and the second end are proximal to the sealed outer perimeter.

Embodiment 10: The oral pouched product according to any of embodiments 1-9, wherein the wall structure forms a lateral perimeter surrounding a periphery of the second compartment such that the entirety of the wall structure is in spaced relation to the sealed outer perimeter.

Embodiment 11: The oral pouched product according to any of embodiments 1-10, wherein the second compartment is contained entirely within the first compartment such that the first compartment surrounds the second compartment.

Embodiment 12: The oral pouched product according to any of embodiments 1-11, wherein the composition within each of the first and second compartments is the same or different.

Embodiment 13: The oral pouched product any of embodiments 1-12, wherein the composition within each of the first and second compartments is different such that the composition within each compartment provides a different functional or sensory experience.

Embodiment 14: The oral pouched product according to any of embodiments 1-13, wherein the composition within the first compartment and the composition within the second compartment comprise a different flavoring agent, a different active ingredient, or both a different flavoring agent and a different active ingredient.

Embodiment 15: The oral pouched product according to any of embodiments 1-14, wherein the composition in the first compartment and the composition in the second compartment each comprise an active ingredient selected from the group consisting of a nicotine component, botanicals, nutraceuticals, stimulants, amino acids, vitamins, cannabinoids, cannabimimetics, terpenes, and combinations thereof.

Embodiment 16: The oral pouched product according to any of embodiments 1-15, wherein the composition in the first compartment and the composition in the second compartment each comprise one or more additives selected from the group consisting of a flavoring agent, a salt, a sweetener, a binding agent, water, a humectant, a buffering agent and/or a pH adjuster, a tobacco material, and combinations thereof.

Embodiment 17: The oral pouched product according to any of embodiments 1-16, wherein the oral pouched product is substantially free of a tobacco material.

Embodiment 18: The oral pouched product according to any of embodiments 1-17, wherein the outer water-permeable pouch comprises one or more of a fleece material and a water dispersible film material.

Embodiment 19: The oral pouched product of embodiment 18, wherein the first compartment and the second compartment are separated by a fully or partially welded seam in the outer water-permeable pouch.

Embodiment 20: The oral pouch product according to any of embodiments 1-19, wherein the outer water-permeable pouch comprises a first layer of fleece material and a second layer of fleece material.

Embodiment 21: The oral pouched product of embodiment 20, wherein the porous pouch further comprises at least one intermediate layer of fleece material separating the two or more compartments.

Embodiment 22: The oral pouched product of embodiment 20, wherein the first layer of fleece material and the second layer of fleece material are different such that the first and second layers of fleece material provide a different functional or sensory experience.

Embodiment 23: The oral pouched product of embodiment 22, wherein the first layer of fleece material includes a different flavoring agent, a different active ingredient, or both a different flavoring agent and a different active ingredient when compared to the second layer of fleece material.

Embodiment 24: The oral pouched product of embodiment 22, wherein the first layer of fleece material exhibits one or more of a different porosity, a different permeability, and a different texture when compared to the second layer of fleece material.

Embodiment 25: The oral pouched product of embodiment 21, wherein the first layer of fleece material, the second layer of fleece material, and the intermediate layer of fleece material are welded together along a perimeter thereof to form an outer seam of the porous pouch.

Embodiment 26: The oral pouched product of embodiment 18, wherein the fleece material comprises fibers selected from the group consisting of conventional cellulosic fibers, cotton fibers, wool fibers, polymer/synthetic-type fibers, and combinations thereof.

Embodiment 27: The oral pouched product of embodiment 18, wherein the water dispersible film material comprises a film forming material selected from the group consisting of film-forming polysaccharides, starches, modified starches, celluloses, modified celluloses, pullulan, pectin, alginate, gums, and combinations thereof.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Figure 1B:
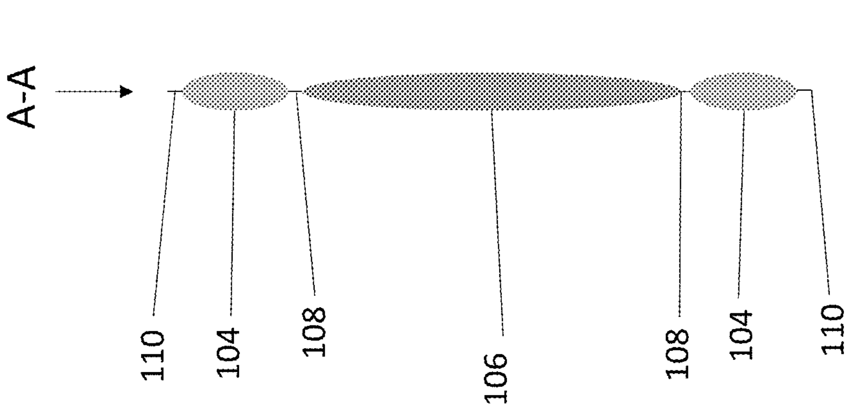

Having thus described aspects of the disclosure in the foregoing general terms, reference will now be made to the accompanying drawing, which is not necessarily drawn to scale. The drawing is exemplary only, and should not be construed as limiting the disclosure.

Figure 1A:
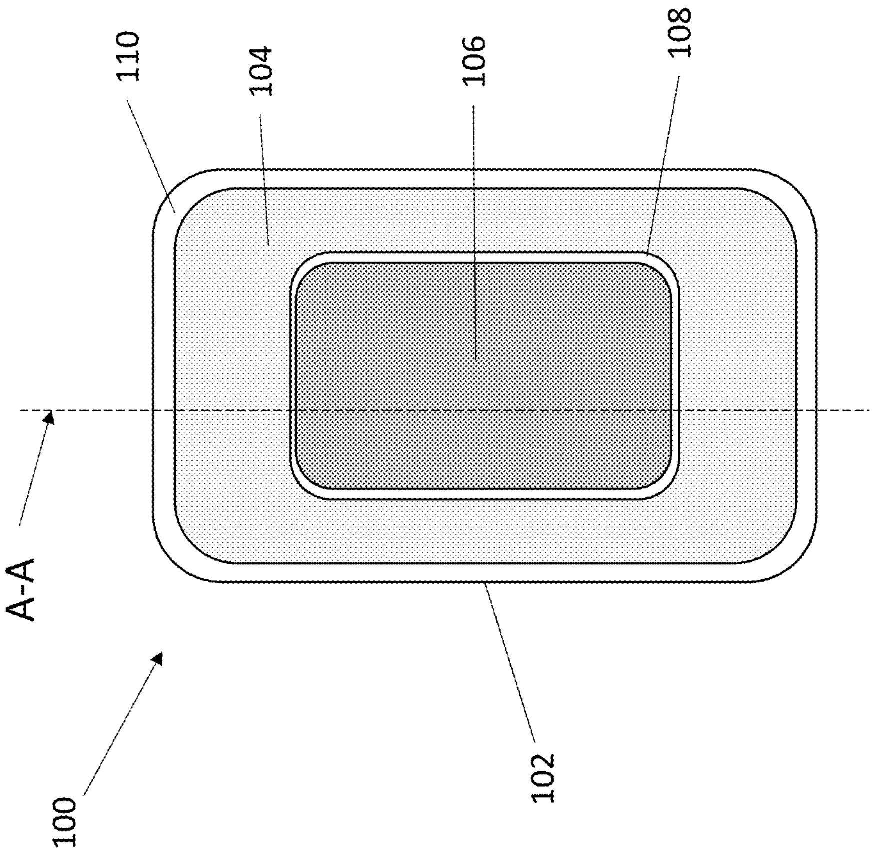
Figure 2:
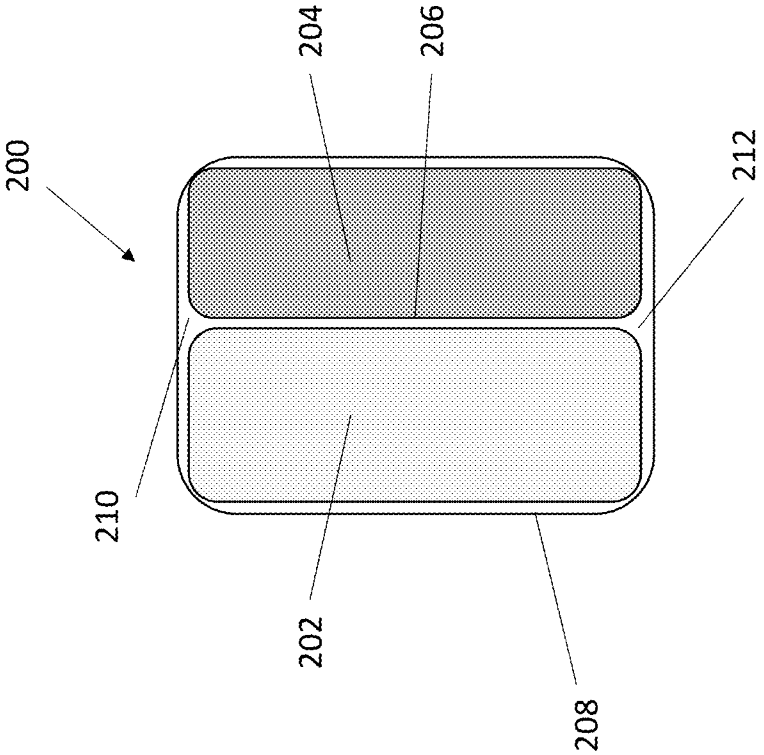
Figure 3C:
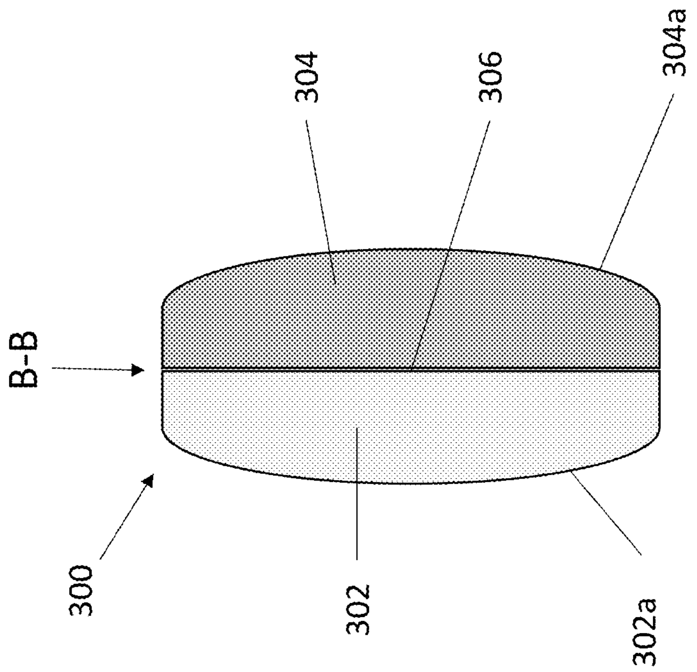
Figure 3B:
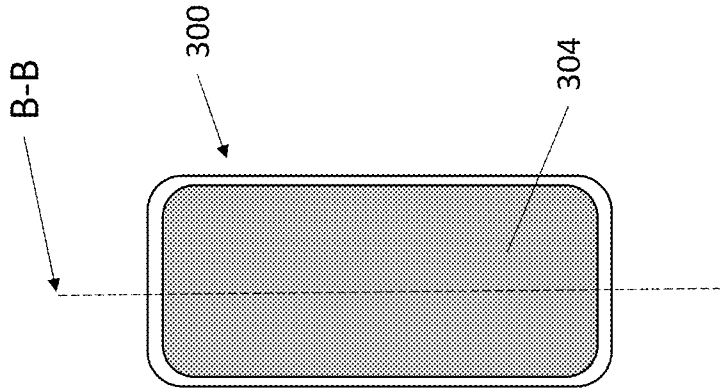
Figure 3A:
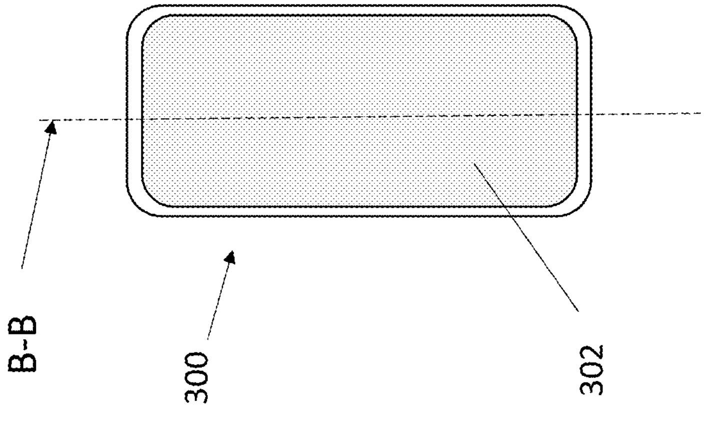
Figure 4B:
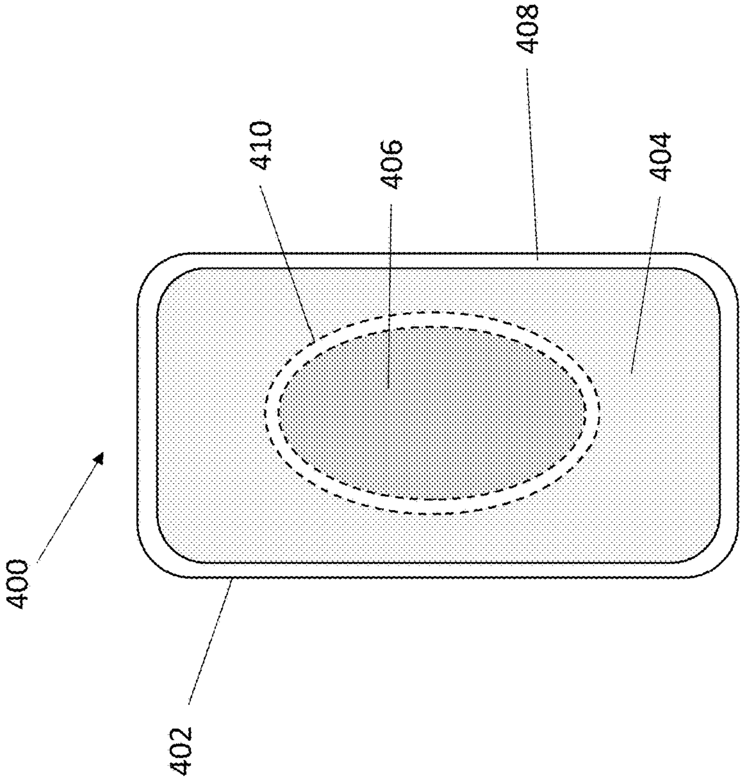
Figure 4A:
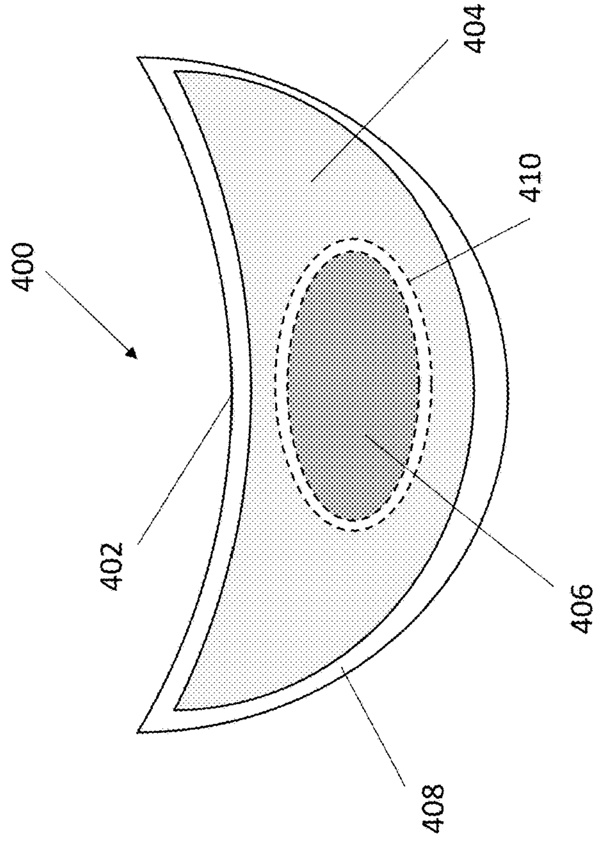

FIG. 1A is a two-dimensional view of an oral pouched product including an outer water-permeable pouch divided into a first compartment and a second compartment, wherein the first compartment and the second compartment are separated by a wall structure, according to an example embodiment of the present disclosure;

FIG. 1B is a two-dimensional side cross-sectional view of the oral pouched product provided in FIG. 1A when viewed perpendicular to the axis A-A, according to an example embodiment of the present disclosure;

FIG. 2 is a two-dimensional view of an oral pouched product including a first compartment and a second compartment arranged in a vertical side-by-side configuration, according to an example embodiment of the present disclosure;

FIG. 3A is a side view of an oral pouched product showing a first compartment thereof when viewed in the direction of the first compartment, according to an example embodiment of the present disclosure;

FIG. 3B is a side view of an oral pouched product showing a second compartment when viewed in the direction of the second compartment, according to an example embodiment of the present disclosure;

FIG. 3C is a two-dimensional side view of the oral pouched product provided in FIGS. 3A and 3B when viewed perpendicular to the axis B-B, according to an example embodiment of the present disclosure;

FIG. 4A is a two-dimensional view of an oral pouched product having an inner compartment substantially in the shape of an ellipse surrounded by an outer compartment substantially in the shape of a rectangle, wherein the inner compartment is contained entirely within the outer compartment, according to an example embodiment of the present disclosure; and FIG. 4B is a two-dimensional view of an oral pouched product having an inner compartment substantially in the shape of an ellipse surrounded by an outer compartment substantially in the shape of crescent, wherein the inner compartment is contained entirely within the outer compartment, according to an example embodiment of the present disclosure.

DETAILED DESCRIPTION

The present disclosure will now be described more fully hereinafter with reference to example embodiments thereof.

These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms “a,” “an,” and “the” include plural referents unless the context clearly dictates otherwise. Reference to “dry weight percent” or “dry weight basis” refers to weight on the basis of dry ingredients (i.e., all ingredients except water). Reference to “wet weight” refers to the weight of the mixture including water. Unless otherwise indicated, reference to “weight percent” of a mixture reflects the total wet weight of the mixture (i.e., including water).

The present disclosure provides compositions configured for oral use and, in particular, multi-compartment oral pouched products including such compositions. For example, some aspects of the present disclosure provide oral pouched products comprising an outer-water permeable pouch divided into two or more compartments (e.g., at least 2 compartments, at least 3 compartments, at least 4 compartments, or more). In some embodiments, the multi-compartment oral products may include a composition configured for oral use within each of the compartments. For example, each compartment may include a composition configured for oral use which, as described herein, may comprise a water soluble component capable of release through the outer water-permeable pouch.

Generally, the configuration and/or arrangement of the compartments within a multi-compartment oral product as described herein may be varied so as to effectively control the functional or sensory experience provided to a user of such products and/or to control the organoleptic properties (e.g., texture, mouth feel, and/or the release profile of components therefrom) of such multi-compartment pouched products. In some embodiments, the products described herein may comprise an outer water-permeable pouch material that surrounds a composition/mixture, also referred to herein as a “material” (e.g., a composition comprising one or more active ingredients and one or more additional components), and such pouched products may be adapted to or configured to provide for controlled release of the one or more components within the material, such as when in contact with the oral cavity of the user of the product.

The disclosure generally provides pouch products that are configured for oral use. The term “configured for oral use” as used herein means that the product is provided in a form such that during use, saliva in the mouth of the user causes one or more of the components of the mixture (e.g., flavoring agents, botanicals, active ingredients, and/or nicotine) to pass into the mouth of the user. In certain embodiments, the product is adapted to deliver components to a user through mucous membranes in the user’s mouth and, in some instances, said component is an active ingredient (including, but not limited to, for example, nicotine) that can be absorbed through the mucous membranes in the mouth when the product is used.

In particular, the disclosure provides products in the form of a material (generally a mixture of one or more components), disposed within a moisture-permeable container (e.g., a water-permeable pouch). As noted herein, in some embodiments, the moisture-permeable container may be subdivided into two or more compartments, each compartment having a separate charge of the material contained therein. Such mixtures in the water-permeable pouch format are typically used by placing a pouch containing the mixture in the mouth of a human subject/user. Generally, the pouch is placed somewhere in the oral cavity of the user, for example under the lips, in the same way as moist snuff products are generally used. The pouch generally is not chewed or swallowed. Exposure to saliva then causes some of the components of the mixture therein (e.g., flavoring agents and/or nicotine) to pass through e.g., the water-permeable pouch and provide the user with flavor and satisfaction, and the user is not required to spit out any portion of the mixture. After about 10 minutes to about 60 minutes, typically about 15 minutes to about 45 minutes, of use/enjoyment, substantial amounts of the mixture have been absorbed through oral mucosa of the human subject, and the pouch may be removed from the mouth of the consumer for disposal. A representative moisture permeable pouch can be composed of a “fleece” type of material in some embodiments of the disclosure as discussed further herein. The orientation, size, and type of pouch material and the type and nature of the material contained therein are not construed as limiting thereof.

Certain embodiments of the disclosure will be described with reference to the figures of the accompanying drawings, and these described embodiments involve oral pouched products having an outer water-permeable pouch and a composition comprising a water-soluble component capable of release through the outer water-permeable pouch (as referenced herein below). As explained in greater detail below, such embodiments are provided by way of example only. In particular, the size and shape of the illustrated outer water-permeable pouches can vary as described in detail herein. The mixture/construction of such packets or pouches, such as the configuration and/or arrangement of two or more compartments within the outer water-permeable pouch and the inclusion of various compositions therein may be varied.

Multi-Compartment Oral Products

Some aspects of the present disclosure provide oral pouched products that are in the form of multi-compartment pouches (e.g., having two or more compartments contained within an outer water-permeable pouch). In some embodiments, the present disclosure provides oral pouched products comprising an outer water-permeable pouch divided into two or more compartments, each of said compartments containing a composition comprising a water-soluble component capable of release through the outer water-permeable pouch. In some embodiments, the multi-compartment pouch products described herein may comprise a first compartment and second compartment. However, such configurations are not intended to be limiting and the multi-compartment oral pouch products of the present disclosure may include one or more additional compartments (e.g., such as a third compartment, a fourth compartment, etc.).

Generally, the configuration and/or arrangement of the compartments within a multi-compartment oral pouch product as described herein may be varied. In some embodiments, for example the embodiment depicted in FIG. 1A, an oral pouched product 100 may comprise an outer water permeable pouch 102 divided into a first compartment 104 and a second compartment 106. In such embodiments, each of said first and second compartments may contain a composition configured for oral use as described herein. As depicted in FIG. 1A, in some embodiments, the first compartment 104 and the second compartment are separated by a wall structure 108. Typically, the wall structure may provide either a nonporous barrier (e.g., that prevents inter-compartment transfer of the composition within each compartment) or a porous barrier (e.g., that allows inter-compartment transfer of the composition contained within each compartment) between the two compartments. In other embodiments, the outer water permeable pouch may comprise one or more additional wall structures to provide an oral pouched product having more than two compartments therein. For example, in some embodiments, the outer water permeable pouch may comprise a first wall structure separating a first compartment and a second compartment, a second wall structure separating the second compartment and a third compartment, and so on.

The configuration of the wall structure separating the first compartment from the second compartment and/or any other compartments may vary. For example, the wall structure may be provided in the form of a fully welded seam (e.g., to provide a nonporous barrier) or a partially welded seam (e.g., to provide a porous barrier) in the outer water-permeable pouch. In some embodiments, a fully welded seam may refer to a seam in the outer water-permeable pouch that has been sealed via application of heat or via any other method of sealing a pouch material that would be sufficient to create a nonporous or substantially impermeable barrier between the compartments. In some embodiments, a partially welded seam may refer to a seam that is perforated or that has been partially sealed via application of heat. Generally, a partially welded seam may refer to any seam that allows at least some degree of inter-compartment transfer of the composition contained within the compartment to another compartment. For example, in some embodiments, a porous seam may be provided between two or more compartments to allow for mixing of the compositions contained within the individual compartment during use, e.g., such mixing being facilitated by mechanical forces, such as chewing, applied to the multi-compartment pouch during use by a user thereof. As depicted in FIG. 1A, the outer water-permeable pouch 102 may also be sealed along the outer perimeter thereof, e.g., forming a sealed outer perimeter 110. The sealing at the outer perimeter of the pouch 102 can be entirely formed by a welded seam resulting from, for example, heat sealing of the outer perimeter of the pouch. In other embodiments, the sealed outer perimeter 110 is only partially defined by a welded seam, such as where the pouch 102 is formed by folding of a pouch material such that only a leading edge and an end edge of the pouch material require welding together to seal the pouch.

FIG. 1B provides a side cross-sectional view of the pouched product provided in FIG. 1A when viewed perpendicular to the axis A-A provided in FIG. 1A. The axis A-A is illustrated in both drawings for clarity purposes. As shown in FIG. 1B, when viewed from the side, the first compartment 104 may be separated from the second compartment 106 by a wall structure or seam 108 in the outer water-permeable pouch 102. The terms "wall structure" and "interior wall structure" are intended to be interchangeable as used herein and generally refer to a physical structure and/or seam that separates the first and second compartment of the multi-compartment pouched products described herein. In addition, the edges (e.g., a leading edge and an end edge of the outer water-permeable pouch in some embodiments, or the entire outer perimeter of the outer water-permeable pouch in other embodiments) of the multi-compartment oral pouched product are formed by the sealed outer perimeter 110. As noted above, the interior wall structure or seam 108 of the pouched product may be in the form of a fully welded seam or a partially welded seam, for example, to provide either a nonporous barrier or a porous barrier between the two compartments, respectively. As shown, the interior wall structure 108 forms a lateral perimeter surrounding a periphery of the second compartment 106 such that the entirety of the interior wall structure is in spaced relation to the sealed outer perimeter 110.

As noted above, the disclosure provides for various configurations of multi-compartment pouches. For example, FIG. 2 depicts an embodiment of a multi-compartment pouch having a side-by-side configuration. In the embodiment depicted in FIG. 2, the oral pouched product 200 comprises a first compartment 202 and a second compartment 204 that are separated by an interior seam/wall structure 206. The oral pouched product 200 also includes a sealed outer perimeter 208. FIG. 2 provides an example of a multi-compartment pouch wherein only a portion of the interior wall structure 206 is spaced from the sealed outer perimeter 208. For example, in the depicted embodiment, the interior wall structure 206 has a first end 210 and a second end 212, and both ends are proximal to the sealed outer perimeter 208.

In one or more embodiments of the present disclosure is provided multi-compartment oral pouched products having a layered configuration (e.g., wherein the two or more compartments are layered on top of each other). In such embodiments, the oral pouched product may comprise an interior wall separating the first compartment from the second compartment and any additional compartments. In embodiments having more than two compartments, the oral pouched product may comprise multiple interior walls separating the individual compartments, for example, a first interior wall separating a first compartment and a second compartment and a second interior wall separating the second compartment and a third compartment, and so on. In some embodiments, the interior wall(s) may be in the form of a water-permeable barrier, e.g., to allow inter-compartment transfer of the composition contained within each compartment. In other embodiments, the interior wall may be in the form of a non-water permeable barrier, e.g., to prevent inter-compartment transfer of the compositions contained within each compartment.

FIGS. 3A, 3B and 3C, for example, depict embodiments of an oral pouched product 300 having a layered configuration. FIG. 3A illustrates a side view of the oral pouched product 300 showing a first compartment 302 (e.g., when viewed in the direction of the first compartment) and FIG. 3B illustrates a side view of the opposite side of the oral pouched product 300 showing a second compartment 304 (e.g., when viewed in the direction of the second compartment). The first compartment 302 and the second compartment 304 are depicted in FIGS. 3A and 3B as separate and distinct layers which can be placed adjacent to each other and separated by an interior wall therebetween. For example, FIG. 3C illustrates a view of the oral pouched product 300 of FIGS. 3A and 3B perpendicular to axis B-B showing the location of an interior wall structure 306 separating the first compartment layer 302 and the second compartment layer 304. The interior wall structure 306 can be constructed of an additional layer of fleece material, such as any of the materials noted herein for use as water-permeable pouch materials.

The interior wall structure 306 can be, for example, affixed to the pouch material forming the exterior of the oral pouched product 300 as explained more fully below. For example, the oral pouched product 300 may be formed of a first layer of fleece material 302*a* and a second layer of fleece material 304*a*. As depicted in FIG. 3C, the outer water-permeable pouch 300 further comprises an interior wall structure 306 formed of an intermediate layer of fleece material. Typically, the first layer of fleece material 302*a*, the second layer of fleece material 304*a*, and the interior wall structure 306 (i.e., the intermediate layer of fleece material) are welded together along a perimeter thereof to form a sealed outer perimeter of the multi-compartment oral pouched product which contains both a first composition within the first compartment and a second composition within the second compartment.

The outer shape and dimensions of the overall product and each individual compartment can vary without departing from the invention. Each compartment can have a different shape and dimensions. FIGS. 4A and 4B illustrate two separate shape configurations of multi-compartment oral products having an inner compartment surrounded by an outer compartment wherein the outer periphery of each compartment has a different shape. In particular, it should be noted that the embodiments depicted in FIGS. 4A and 4B are intended to provide an illustration of multi-compartment pouches having an inner compartment surrounded completely by an outer compartment as demonstrated by the dashed lines surrounding the inner compartment. FIGS. 4A and 4B illustrate oral pouched products 400 comprising an outer water-permeable pouch 402 divided into a first, outer compartment 404 and a second, inner compartment 406. In some embodiments, the multi-compartment oral pouched product may further comprise a sealed outer perimeter 408 adjacent to the first, outer compartment 404 and an interior wall structure 410 separating the first, outer compartment 404 from the second, inner compartment 406. The interior wall structure 410 forms a lateral perimeter surrounding a periphery of the second, inner compartment 406 such that the entirety of the interior wall structure is in a spaced relation to the sealed outer perimeter 408.

The exact shapes of pouches and/or compartments provided within the pouches are not particularly limited. In certain embodiments, shaped pouches provided herein comprise at least one rounded dimension/edge. Various shapes can be described, for example, as square, rectangular, circular, oval, oblong, crescent-shaped, rounded crescent-shaped, half-moon-shaped, half-circular, teardrop-like, star-shaped, domed, rhombic, rounded rhombic, diamond-shaped, rounded diamond-shaped, kidney-shaped, heart-shaped, triangular, rounded triangular (including, e.g., isosceles, equilateral, scalene, acute, right, and obtuse) hexagonal, rounded hexagonal (including hexagonal with equal length edges and with varying length edges) and the like.

The overall dimensions of the pouch and the dimensions of each compartment can vary. Typically, the oral products of the disclosure will have all three dimensions (length, width, and depth) in the range of 0.1 to about 60 mm. The dimensions of the individual compartments of the oral product of the disclosure can also vary. In certain embodiments, the volume of each compartment can be expressed as a percentage of the overall interior volume of the oral product. For example, in certain embodiments, each compartment (regardless of the number of compartments) will each comprise between 1% and 99% of the total volume of the oral product. In certain embodiments, each compartment will comprise between 20% and 80% of the total volume of the oral product, such as about 25% to about 75% or about 30% to about 60%.

Pouch Materials

In some embodiments of the present disclosure, the outer water-permeable pouch material, including the two or more compartments provided therein, may be formed of a fleece material, e.g., wherein the fleece material may be in the form of a fleece fabric material, such as in the form of a woven or nonwoven fabric comprising a plurality of fibers. In other embodiments, the outer water-permeable pouch may comprise multiple fleece materials that have been welded together. In such embodiments, the product may comprise a unitizing structure wherein the fleece material is in the form of a multi-compartment pouch that contains a material within each compartment, for example, as would typically be provided in a traditional pouched product or the like. "Fleece materials" as referred to herein may be in the form of a fleece fabric material, such as in the form of a woven or nonwoven fabric comprising a plurality of fibers.

As used herein, the term "fiber" is defined as a basic element of textiles. Fibers are often in the form of a rope- or string-like element. As used herein, the term "fiber" is intended to include fibers, filaments, continuous filaments, staple fibers, and the like. In some embodiments, the fleece materials described herein may comprise multicomponent fibers. The term "multicomponent fibers" refers to fibers that comprise two or more components that are different by physical or chemical nature, including bicomponent fibers. Specifically, the term "multicomponent fibers" includes staple and continuous fibers prepared from two or more polymers present in discrete structured domains in the fiber, as opposed to blends where the domains tend to be dispersed, random or unstructured.

The term "nonwoven" is used herein in reference to fibrous materials, webs, mats, bans, or sheets in which fibers are aligned in an undefined or random orientation. The nonwoven fibers are initially presented as unbound fibers or filaments. An important step in the manufacturing of nonwovens involves binding the various fibers or filaments together. The manner in which the fibers or filaments are bound can vary, and include thermal, mechanical and chemical techniques that are selected in part based on the desired characteristics of the final product, as discussed in more detail herein below.

In some embodiments, fleece materials of the present disclosure may be formed from various types of fibers (e.g., conventional cellulosic fibers (e.g., such as viscose fibers, regenerated cellulose fibers, cellulose fibers, and wood pulps), cotton fibers, wool fibers, hemp fibers, other natural fibers, polymer/synthetic-type fibers, and combinations thereof) capable of being formed into a traditional fleece fabrics or other traditional pouch materials. For example, fleece materials may be provided in the form of a woven or nonwoven fabric. Suitable types of fleece materials, for example, are described in U.S. Pat. No. 8,931,493 to Sebastian et al.; US Pat. Appl. Pub. Nos. 2016/0000140 to Sebastian et al. and 2016/0073689 to Sebastian et al.; which are all incorporated herein by reference. In some embodiments, the fibers within the fleece material may include, but are not limited to, a polymer selected from the group consisting of polyglycolic acid, polylactic acid, polyhydroxyalkanoates, polycaprolactone, polybutylene succinate, polybutylene succinate adipate, and copolymers thereof. In some embodiments, the fibers within the fleece material may be selected from the groups consisting of cellulose fibers, viscose fibers, regenerated cellulose fibers, other wood fibers, hemp fibers, and the like. In various embodiments, the fibers within the fleece material can comprise polyester fibers. As is known in the art, polyester is a category of polymer that contains the ester functional group in the main chain. Polyesters include naturally occurring polymers (e.g., cutin of plant cuticles), as well as synthetically produced polymers (e.g., polybutyrate). Certain exemplary polyesters that can be incorporated, in fiber form, within the disclosed pouches include, but are not limited to, cutin, polybutyrate, poly(ethylene terephthalate), polyglycolide, polylactic acid, polycaprolactone, polyhydroxyalkanoate, polyhydroxybutyrate, and copolymers and derivatives thereof. Natural polyesters and certain synthetic polyesters are biodegradable. Accordingly, using certain polyester fibers in the pouch materials described herein can enhance the biodegradability of the pouched product.

Nonwoven fabric forming methods for natural and synthetic fibers may include drylaid, airlaid and wetlaid methods. In some embodiments, the nonwoven fabric can be formed using a spunlaid or spunmelt process, which includes both spunbond and meltblown processes, wherein such processes are understood to typically entail melting, extruding, collecting and bonding thermoplastic polymer materials to form a fibrous nonwoven web. The technique of meltblowing is known in the art and is discussed in various patents, for example, U.S. Pat. No. 3,849,241 to Butin, U.S. Pat. No. 3,987,185 to Buntin et al., U.S. Pat. No. 3,972,759 to Buntin, and U.S. Pat. No. 4,622,259 to McAmish et al., each of which is herein incorporated by reference in its entirety. General spunbonding processes are described, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al., which are all incorporated herein by reference.

The arrangement and/or configuration of fibers used in the fleece materials can vary, and include fibers having any type of cross-section, including, but not limited to, circular, rectangular, square, oval, triangular, and multilobal. In some embodiments, the fibers can have one or more void spaces, wherein the void spaces can have, for example, circular, rectangular, square, oval, triangular, or multilobal cross-sections. As noted previously, the fibers can be selected from single-component (i.e., uniform in composition throughout the fiber) or multicomponent fiber types including, but not limited to, fibers having a sheath/core structure and fibers having an islands-in-the-sea structure, as well as fibers having a side-by-side, segmented pie, segmented cross, segmented ribbon, or tipped multilobal cross-sections.

In some embodiments, the types of fleece materials used to form multi-compartment pouches as described herein may be varied to provide a specific functional or sensory experience to a user thereof. In some embodiments, for example, two or more different types of fleece materials may be used in forming multi-compartment pouches according to the disclosure. In such embodiments, the individual fleece materials may have one or more different physical properties (e.g., texture, basis weight, porosity, permeability, etc.) and/or may include one or more additives contained therein (e.g., flavoring agents, active ingredients, or other additives) which impart different functional or sensory characteristics on the product during use. It should be noted that fleece materials suitable for use in the present disclosure may include any active ingredient and/or flavoring and/or other additive described herein with respect to the compositions contained within the individual compartments of the pouch. In one or more embodiments, fleece materials as described herein may include one or more additives therein that are releasable therefrom in response to a certain stimulus, e.g., when in contact with the oral cavity of a user or upon a certain minimum mechanical force applied to the product by the user, e.g., chewing or working the product in the oral cavity. The additives contained with said fleece materials can be adapted to or configured to absorb, adsorb, or otherwise become directly entrained/embedded within the porous structure of the fleece material. In this manner, the releasable additives may be retained with a desired level of stability and/or may be configured for controlled release from the naturally porous structure of the fleece material during use. Further, certain fleece materials containing additives therein may be adapted for enhancing one or more sensory characteristics of the product, such as taste, mouthfeel, moistness, coolness/heat, and/or fragrance.

The fleece materials described herein can have varying thicknesses, porosities and other parameters. The fleece material can be formed such that the fiber orientation and porosity of the pouched product formed therefrom can retain the composition adapted for oral use that is enclosed within the outer water-permeable pouch, but can also allow the flavors of the composition to be enjoyed by the consumer. For example, in some embodiments, the fleece material can have a basis weight of about 20 gsm to about 35 gsm, and in some such embodiments about 25 gsm to about 30 gsm. In certain embodiments, the fleece material can have a basis weight of about 28 gsm. In some embodiments, the fleece material can have a relatively high basis weight. For example, the basis weight of a fleece material can be in the range of about 25-40 gsm, about 30-40 gsm, or about 35-40 gsm. In certain embodiments, the basis weight of the fleece material can be about 25 gsm or greater, about 30 gsm or greater, or about 35 gsm or greater. Basis weight of a fabric can be measured using ASTM D3776/D3776M-09a (2013) (Standard Test Methods for Mass Per Unit Area (Weight) of Fabric), for example.

In various embodiments, the fleece material can have a thickness of about 0.1 mm to about 0.15 mm (e.g., about 0.11 mm). The fleece material can have an elongation of about 70% to about 80%, e.g., about 78%. In some embodiments, the fleece material can have a peak load of about 4 lbs. to about 8 lbs., e.g., about 5.5 lbs. Elongation and breaking strength of textile fabrics can be measured using ASTM D5034-09(2013) (Standard Test Method for Breaking Strength and Elongation of Textile Fabrics (Grab Test)), for example. In various embodiments, the fleece material can have a Tensile Energy Absorption (TEA) of about 35 to about 40, e.g., about 37. In certain embodiments, the fleece material can have a porosity of greater than about 10,000 ml/min/cm$^2$. TEA can be measured, for example, as the work done to break the specimen under tensile loading per lateral area of the specimen. Porosity, or air permeability of textile fabrics can be measured using ASTM D737-04(2012) (Standard Test method for Air Permeability of Textile Fabrics), for example.

As noted above, altering the physical properties (e.g., texture, basis weight, porosity, permeability, etc.) of a fleece material may affect the functional or sensory characteristics of the products described herein. For example, by controlling the basis weight of the fleece material the thickness and/or density of the fleece material may also be affected or altered. Fleece materials according to the present disclosure may be defined herein with respect to their "basis weight," "density," and/or "thickness." Such terms are meant to be understood according to their typical meanings in the context of production of textile and nonwoven materials generally. Various combinations of such parameters may be varied in order to provide fleece materials and oral products produced therefrom, with varying organoleptic properties and/or dissolution profiles. For example, use of fleece materials having a high basis weight and/or high thickness may provide increased durability (e.g., the ability to hold together when chewed or worked within the mouth of a user) when compared to fleece materials having lower basis weights. In addition, selection of a fleece material with a certain basis weight can provide certain textural characteristics, e.g., such as increased or decreased softness or rigidity. Likewise, altering the porosity and/or the air permeability of certain fleece materials can affect the dissolution and/or release profile of the composition in the pouch and/or one or more additives in the fleece material.

Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). The components of such water-dispersible films can vary. Typically, water dispersible films as described herein comprise various film-forming materials. Example film-forming materials can include, e.g., film-forming polysaccharides, starch, modified corn starch, modified celluloses, pullulan, pectin, alginate (including, e.g., cross-linked alginate), gums, and other film formers, e.g., natural film formers. In certain embodiments, water dispersible films as described herein may include, in particular, a binder component and a plasticizer component.

Certain specific examples of modified celluloses that can be employed as components of the binder include, but are not limited to, hydroxypropylmethyl cellulose (HPMC), methyl cellulose, and carboxymethylcellulose. In some embodiments, two or more HPMCs are employed. HPMCs can vary, e.g., by viscosity, particle properties, polymer molecular weight, and by average content of methoxy groups and average content of hydroxpropyl groups, as well as substitution pattern. HPMC binders that can be employed suitably in the disclosed products are not particularly limited. Various types of HPMC are available, e.g., from JRS Pharma (e.g., Vivapharm® HPMC, e.g., grade E5), Dow (e.g., Methocel™, e.g., grade K99), Lotte Fine Chemical (e.g., AnyAddy® HPMC), and others, which are also encompassed by the present disclosure.

Modified corn starches can include, e.g., chemically modified starches (e.g., OSA starch) and acid-modified starch. Certain specific examples of modified corn starches that can be employed include, but are not limited to, corn starches that have been treated to improve the consistency thereof, e.g., corn starch that has been roasted, treated with acid, treated with an electrical starch, or treated with sodium hydroxide or potassium hydroxide. In particular, corn starches that form a film when dried are applicable as binders according to the present disclosure; a modified starch can be selected in some embodiments to give desired mechanical, tactile, and/or sensory properties (for example flexibility, low tack, neutral sensory characteristics). In other embodiments, these properties can be modified by the other components of the composition. One particular starch that can be employed according to the present disclosure is Pure Cote® B792, available from Grain Processing Corporation, which is an acid-hydrolyzed starch that was designed for producing clear, flexible films without heating to hydrate the starch.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof.

Plasticizers are typically incorporated into water-dispersible films to promote softness and/or flexibility therein. Without being limited by theory, it is believed the plasticizer can act to facilitate hydration within the film. Examples of suitable plasticizers include, but are not limited to, organic non-polymeric materials. Certain non-limiting plasticizers comprise glyceryl monostearate, triethyl citrate, glycerin, polyethylene glycol, propylene glycol, and combinations thereof. In various embodiments, the plasticizer is selected from the group consisting of glycerin, propylene glycol, and combinations thereof.

Preferred pouch materials, though water dispersible or dissolvable, may be designed and manufactured such that under conditions of normal use, a significant amount of the composition contents permeate through the pouch material prior to the time that the pouch undergoes loss of its physical integrity.

As noted above, some aspects of the present disclosure provide multi-compartment oral pouch products comprising an outer water-permeable pouch, which may be formed of a fleece material and/or a water dispersible film material. In some embodiments, for example, the outer water-permeable pouch may be subdivided into two or more compartments to provide a first compartment and a second compartment. In such embodiments, the two or more compartments may be separated by a wall structure within the outer water-permeable pouch. For example, in some embodiments, the wall structure may be in the form of a fully welded seam or a partially welded seam in the fleece material and/or a fully or partially sealed seam in the water-dispersible film material. As noted herein, the interior seam in the outer water-permeable pouch material may be formed using any method commonly known in the art (e.g., heat sealing, mechanical perforation, vacuum sealing, etc.).

Organoleptic Properties and Release Profile

As noted herein above, the configuration and/or arrangement of the compartments within a multi-compartment oral product and/or the inclusion of different compositions within separate compartments of such products and/or the types of fleece materials employed may be varied so as to effectively control the functional or sensory experience provided to a user of such products and/or to control the organoleptic properties (e.g., texture, mouth feel, and/or the release profile of components therefrom) of such multi-compartment pouched products. For example, in some embodiments, the products described herein may comprise an outer water-permeable pouch having two or more compartments, each, individually, configured to contain a composition/mixture, also referred to herein as a "material" (e.g., a composition comprising one or more active ingredients and one or more additional components), and such pouched products may be adapted to or configured to provide for controlled release of the one or more components within the material, such as when in contact with the oral cavity of the user of the product.

In some embodiments, for example, the composition contained within the first compartment and the composition contained within the second compartment may be substantially the same. In other embodiments, the composition contained within the first compartment and the composition contained within the second compartment may be different. In some embodiments, for example, the composition within the first compartment and the composition within the second compartment may include a different flavoring agent, a different active ingredient, or both a different flavoring agent and a different active ingredient. In some embodiments, the composition within one or more of the compartments may also include one or more additives. In some embodiments, the composition within the first compartment and the composition within the second compartment may include a different additive in addition to, or alternate to, a different flavoring agent and/or active ingredient. Advantageously, by providing a different composition (e.g., having one or more of a different flavoring agent, active ingredient, or other additive) within the two or more compartments, the individual composition within each compartment can provide a different functional or sensory experience to a user. As used herein, two or more compositions providing a "different functional or sensory" experience may include, but are not limited to, providing one or more different active ingredients as described herein (e.g., nicotine, caffeine, vitamins, botanicals, terpenes, stimulants, antioxidants, cannabinoids, etc.) and/or providing one or more different flavoring agents as described herein, and/or providing one or more different physical properties (e.g., such as texture (e.g., softness, stiffness, firmness, hardness, stickiness, fluffiness, durability, chewability, workability), porosity, dissolvability, permeability, and the like). In some embodiments, for example, each composition in the two or more compartments may, individually, provide one or more of a sweet, salty, sour, spicy, hot, cool, fresh, fruity, and/or minty sensation to a user.

In some embodiments, the configuration of the two or more compartments within the outer water-permeable pouch and/or the inclusion of a specific composition within each of the two or more compartments may be varied to alter the dissolution or release profile of one or more components from the composition. As discussed herein, various components may be included in the materials/compositions that are incorporated into the multi-compartment oral pouched products described herein. For example, combinations of flavoring agents and/or active ingredients may be incorporated into the pouched products disclosed herein and the release profile of such ingredients therefrom can be controlled by altering the arrangement of the two or more compartments and/or by providing a different composition within each compartment. "Release profile" as referred to herein is meant to define the amount of time it takes to deliver one or more components within the composition/material to a user through mucous membranes in the user's mouth, for example, in some instances said ingredients (including, but not limited to, for example, nicotine) can be absorbed directly through the mucous membranes in the mouth when the product is used. For example, as described herein below, various configurations of the products disclosed herein may provide for the active ingredient to be delivered to a user of the product in a relatively short period of time (e.g., "rapid release") upon insertion of the product in the oral cavity, or the active ingredient may be released more slowly over time during use of the product by the user (e.g., "delayed release").

In some embodiments, the presence of both an active ingredient configured for rapid release in one compartment of the multi-compartment pouch and an active ingredient configured for delayed release in another compartment of the multi-compartment pouch may provide for an "extended" release product that releases the active ingredients therein continuously over the life of the product. In some embodiments, the presence of a one or more additives within the composition may alter the release profile of one or more components (e.g., a flavoring agent, an active ingredient, or other additive) therein and, thus, one or more additives may be added individually to the composition in any individual compartment so as to vary the release profile of that specific composition to the user. In still other embodiments, the presence of both a flavoring agent configured for rapid release in one compartment of the multi-compartment pouch and a flavoring agent configured for delayed release in another compartment of the multi-compartment pouch may provide for an "extended" release product that releases the active ingredients therein continuously over the life of the product. Generally, the amount of time required for a substantial amount of the one or more components to be absorbed directly through the mucous membranes in the mouth of the user may be in the range of about 1 minute to about 60 minutes, about 5 minutes to about 45 minutes, or about 10 minutes to about 30 minutes after insertion of the pouched product into the oral cavity of a user.

In still other embodiments, the selection of one or more different types of fleece materials (e.g., having one or more different characteristics) for use in forming multi-compartment pouches may be varied to alter the dissolution or release profile of one or more components from the compositions contained therein and/or to alter the dissolution or release profile of one or more additives contained within the fleece material itself. As discussed herein, various additives (e.g., flavoring agent, active ingredient, or other additive) may be included within fleece materials using various means (e.g., via encapsulation, absorbing or adsorbing the additives on the fleece material, and other methods) and such additive containing fleece materials can be incorporated into the multi-compartment oral pouched products described herein. For example, combinations of flavoring agents and/or active ingredients may be incorporated into the fleece materials disclosed herein and the release profile of such ingredients therefrom can be controlled by altering the basis weight, porosity, and/or permeability of the fleece materials. Likewise, multiple layers of fleece materials having different characteristics may be used to provide a different functional or sensory experience. In certain embodiments, a first layer of fleece material and a second layer of fleece material may be used to form a multi-compartment pouch as described more fully herein. In such embodiments, the first layer of fleece material and the second layer of fleece material may be different such that the first and second layers of fleece material provide a different functional or sensory experience. For example, in some embodiments, the first layer of fleece material may include a different flavoring agent, a different active ingredient, or both a different flavoring agent and a different active ingredient when compared to the second layer of fleece material. It should also be understood that any other additives suitable for use in the compositions described herein may also be incorporated directly into one or more layers of fleece materials, e.g., including, but not limited to, salts, sweeteners, organic acids, basic amines, binders, humectants, colorants, and/or pH adjusters or buffering agents as described herein below. In some embodiments, the first layer of fleece material can exhibit one or more of a different porosity, a different permeability, and a different texture when compared to the second layer of fleece material.

The foregoing discussion provides non-limiting examples of configurations that can provide for desired release profiles, including one or more of: fast release or rapid release; slow release or extended release; delayed release; and the like. The release profile may be at least partially controlled by any one or more of the chemical nature of the active ingredient, the physical state of the active ingredient in the composition/product, a carrier/filler with which the active ingredient is combined (e.g., absorbed or adsorbed thereon), and solubility of the active ingredient. The percentages described with regard to the release rates noted above are referred to as being by weight based on the total weight of the oral composition.

Material within the Pouch

As noted above, pouched products generally comprise, in addition to the pouch-based exterior, a material within the pouch that typically comprises one or more active ingredients and/or one or more flavorants, and various other optional ingredients. The composition of the material within the pouches provided herein is not particularly limited, and can comprise any filling composition, including those included within conventional pouched products. Such compositions are generally mixtures of two or more components and as such, the compositions are, in some cases, referenced herein below as "mixtures." Certain components that can advantageously be included in the mixtures within certain embodiments of the pouched products provided herein are outlined generally below; however, it is to be understood that the discussion below is not intended to be limiting of the components that can be incorporated within the disclosed pouched products. In addition, as previously noted herein, the individual composition provided within each compartment of the multi-compartment oral products described herein may vary. For example, the composition within a single compartment may be the same as or may be different from the composition provided in any additional compartment provided with the disclosed products.

Active Ingredient

The material or composition as disclosed herein includes one or more active ingredients. As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

In certain embodiments, the active ingredient is selected from the group consisting of caffeine, taurine, GABA, theanine, vitamin C, lemon balm extract, ginseng, citicoline, sunflower lecithin, and combinations thereof. For example, the active ingredient can include a combination of caffeine, theanine, and optionally ginseng. In another embodiment, the active ingredient includes a combination of theanine, gamma-amino butyric acid (GABA), and lemon balm extract. In a further embodiment, the active ingredient includes theanine, theanine and tryptophan, or theanine and one or more B vitamins (e.g., vitamin B6 or B12). In a still further embodiment, the active ingredient includes a combination of caffeine, taurine, and vitamin C.

In some embodiments, the active ingredient as described herein may be sensitive to degradation (e.g., oxidative, photolytic, thermal, evaporative) during processing or upon storage of the oral product. In such embodiments, the active ingredient (such as caffeine, vitamin A, and iron (Fe)) may be encapsulated, or the matrix otherwise modified with fillers, binders, and the like, to provide enhanced stability to the active ingredient. For example, binders such as functional celluloses (e.g., cellulose ethers including, but not limited to, hydroxypropyl cellulose) may be employed to enhance stability of such actives toward degradation. Additionally, encapsulated actives may need to be paired with an excipient in the composition to increase their solubility and/or bioavailability. Non-limiting examples of suitable excipients include beta-carotene, lycopene, Vitamin D, Vitamin E, Co-enzyme Q10, Vitamin K, and curcumin.

The particular percentages of active ingredients present will vary depending upon the desired characteristics of the particular product. Typically, an active ingredient or combination thereof is present in a total concentration of at least about 0.001% by weight of the material, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the material. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the material. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). In some embodiments, the compositions as disclosed herein can be characterized as free of any tobacco material (e.g., any embodiment as disclosed herein may be completely or substantially free of any tobacco material). By "substantially free" is meant that no tobacco material has been intentionally added. For example, certain embodiments can be characterized as having less than 0.001% by weight of tobacco, or less than 0.0001%, or even 0% by weight of tobacco.

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the material.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, *Bacopa monniera*, baobab, basil, *Centella asiatica*, Chai-hu, chamomile, cherry blossom, chlorophyll, cinnamon, citrus, cloves, cocoa, cordyceps, curcumin, damiana, *Dorstenia arifolia, Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, cannabis, hemp, hops, jasmine, *Kaempferia parviflora* (Thai ginseng), kava, lavender, lemon balm, lemongrass, licorice, lutein, maca, matcha, *Nardostachys chinensis*, oil-based extract of *Viola odorata*, peppermint, quercetin, resveratrol, *Rhizoma gastrodiae, Rhodiola, rooibos*, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and *Yerba mate.*

In some embodiments, the active ingredient comprises lemon balm. Lemon balm (*Melissa officinalis*) is a mildly lemon-scented herb from the same family as mint (Lamiaceae). The herb is native to Europe, North Africa, and West Asia. The tea of lemon balm, as well as the essential oil and the extract, are used in traditional and alternative medicine. In some embodiments, the active ingredient comprises lemon balm extract. In some embodiments, the lemon balm extract is present in an amount of from about 1 to about 4% by weight, based on the total weight of the material.

In some embodiments, the active ingredient comprises ginseng. Ginseng is the root of plants of the genus *Panax*, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the ginseng is American ginseng or Korean ginseng. In specific embodiments, the active ingredient comprises Korean ginseng. In some embodiments, ginseng is present in an amount of from about 0.4 to about 0.6% by weight, based on the total weight of the material.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the material. In some embodiments, the composition comprises caffeine in an amount of from about 1.5 to about 6% by weight, based on the total weight of the material;

Amino Acids

In some embodiments, the active ingredient comprises an amino acid. As used herein, the term "amino acid" refers to an organic compound that contains amine ($—NH_2$) and carboxyl (—COOH) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine. In some embodiments, the active ingredient comprises theanine. In some embodiments, the active ingredient comprises GABA. In some embodiments, the active ingredient comprises a combination of theanine and GABA. In some embodiments, the active ingredient is a combination of theanine, GABA, and lemon balm. In some embodiments, the active ingredient is a combination of caffeine, theanine, and ginseng. In some embodiments, the active ingredient comprises taurine. In some embodiments, the active ingredient is a combination of caffeine and taurine.

When present, an amino acid or combination of amino acids (e.g., theanine, GABA, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the material.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine.

When present, a vitamin or combination of vitamins (e.g., vitamin B6, vitamin B12, vitamin E, vitamin C, or a combination thereof) is typically at a concentration of from about 0.01% w/w to about 6% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, about 1%, about 2%, about 3%, about 4%, about 5%, or about 6% by weight, based on the total weight of the material.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, *Gingko biloba*, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, *Yerba mate, Yerba santa, Bacopa monniera, Withania somnifera*, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the material.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the material, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the material. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the material.

In some embodiments, the products or compositions of the disclosure can be characterized as free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component).

Cannabinoids

In some embodiments, the active ingredient comprises one or more cannabinoids. As used herein, the term "cannabinoid" refers to a class of diverse natural or synthetic chemical compounds that acts on cannabinoid receptors (i.e., CB1 and CB2) in cells that alter neurotransmitter release in the brain. Cannabinoids are cyclic molecules exhibiting particular properties such as the ability to easily cross the blood-brain barrier. Cannabinoids may be naturally occurring (Phytocannabinoids) from plants such as cannabis, (endocannabinoids) from animals, or artificially manufactured (synthetic cannabinoids). Cannabis species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof. In some embodiments, the cannabinoid comprises at least tetrahydrocannabinol (THC). In some embodiments, the cannabinoid is tetrahydrocannabinol (THC). In some embodiments, the cannabinoid comprises at least cannabidiol (CBD). In some embodiments, the cannabinoid is cannabidiol (CBD). In some embodiments, the CBD is synthetic CBD. Notably, CBD has a log P value of about 6.5, making it insoluble in an aqueous environment (e.g., saliva).

In some embodiments, the cannabinoid (e.g., CBD) is added to the oral product in the form of an isolate. An isolate is an extract from a plant, such as cannabis, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the oral product is no greater than about 1% by weight of the oral product, such as no greater than about 0.5% by weight of the oral product, such as no greater than about 0.1% by weight of the oral product, such as no greater than about 0.01% by weight of the oral product.

The choice of cannabinoid and the particular percentages thereof which may be present within the disclosed oral product will vary depending upon the desired flavor, texture, and other characteristics of the oral product.

Alternatively, or in addition to the cannabinoid, the lipophilic active agent may include a cannabimimetic, which is a class of compounds derived from plants other than cannabis that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

When present, a cannabinoid (e.g., CBD) or cannabimimetic is typically in a concentration of at least about 0.1% by weight of the composition, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition. In some embodiments, the cannabinoid (such as CBD) is present in the oral product in a concentration of at least about 0.001% by weight of the oral product, such as in a range from about 0.001% to about 2% by weight of the oral product. In some embodiments, the cannabinoid (such as CBD) is present in the oral product in a concentration of from about 0.1% to about 1.5% by weight, based on the total weight of the oral product. In some embodiments, the cannabinoid (such as CBD) is present in a concentration from about 0.4% to about 1.5% by weight, based on the total weight of the oral product.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the active ingredient comprises more than one terpene. For example, the active ingredient may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the material.

In some embodiments, the composition is substantially free of any API. By "substantially free of any API" means that the composition does not contain, and specifically excludes, the presence of any API as defined herein, such as any Food and Drug Administration (FDA) approved therapeutic agent intended to treat any medical condition.

Flavoring Agent

In some embodiments, the material or composition comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. In some embodiments, the material may include a single flavoring agent or a plurality of flavoring agents. If desired, one or more flavoring agents may be embedded within the fleece material, absorbed in or adsorbed on at least one surface of the fleece material, or impregnated within the fleece material.

Non-limiting examples of flavoring agents can include vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, terpenes, trigeminal sensates, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as *eucalyptus*. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent may be a volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin.

Filler

The material or composition as described herein may include at least one particulate filler component. Such particulate fillers may fulfill multiple functions, such as enhancing certain organoleptic properties such as texture and mouthfeel, enhancing cohesiveness or compressibility of the product, and the like. Generally, the fillers are porous particulate materials and are cellulose-based. For example, suitable particulate fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential particulate fillers include maltodextrin, dextrose, calcium carbonate, calcium phosphate, lactose, mannitol, xylitol, and sorbitol. Combinations of fillers can also be used.

“Starch” as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the mixture based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be “genetically modified” starches. Other starches are obtained and subsequently modified by chemical, enzymatic, or physical means. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

In some embodiments, the particulate filler component is a cellulose material or cellulose derivative. One particularly suitable particulate filler component for use in the products described herein is microcrystalline cellulose (“MCC”). The MCC may be synthetic or semi-synthetic, or it may be obtained entirely from natural celluloses. The MCC may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the mixture comprises MCC as the particulate filler component. The quantity of MCC present in the mixture as described herein may vary according to the desired properties.

The amount of particulate filler can vary, but is typically up to about 75 percent of the material by weight, based on the total weight of the material. A typical range of particulate filler (e.g., MCC) within the material can be from about 10 to about 75 percent by total weight of the mixture, for example, from about 10, about 15, about 20, about 25, or about 30, to about 35, about 40, about 45, or about 50 weight percent (e.g., about 20 to about 50 weight percent or about 25 to about 45 weight percent). In certain embodiments, the amount of particulate filler is at least about 10 percent by weight, such as at least about 20 percent, or at least about 25 percent, or at least about 30 percent, or at least about 35 percent, or at least about 40 percent, based on the total weight of the material.

In one embodiment, the particulate filler further comprises a cellulose derivative or a combination of such derivatives. In some embodiments, the mixture comprises from about 1 to about 10% of the cellulose derivative by weight, based on the total weight of the mixture, with certain embodiments comprising about 1 to about 5% by weight of cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose (“HPC”), hydroxypropylmethylcellulose (“HPMC”), hydroxyethyl cellulose, and carboxymethylcellulose (“CMC”). In one embodiment, the cellulose derivative is one or more of methylcellulose, HPC, HPMC, hydroxyethyl cellulose, and CMC. In one embodiment, the cellulose derivative is HPC. In some embodiments, the mixture comprises from about 1 to about 3% HPC by weight, based on the total weight of the material.

Tobacco Material

In some embodiments, the material or composition of the oral pouched product may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N.*

*setchelli, N. sylvestris, N. tomentosa, N. tomentosiformis, N. undulata, N.* x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *hersperis, N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a mixture as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The material disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the material typically includes tobacco lamina, or a tobacco lamina and stem mixture (of which at least a portion is smoke-treated). Portions of the tobaccos within the material may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the material optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Typically, plant parts or pieces are comminuted, ground or pulverized into a particulate form using equipment and techniques for grinding, milling, or the like. Often, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. For example, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral products, it is typical for a harvested plant of the *Nicotiana* species to be subjected to a curing process. The tobacco materials incorporated within the material for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int,* 21, 305-320 (2005) and Staaf et al., *Beitrage Tabakforsch. Int,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat.

No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the final mixture, with an example range of up to about 30% by weight (or up to about 20% by weight or up to about 10% by weight or up to about 5% by weight), based on total weight of the mixture (e.g., about 0.1 to about 15% by weight).

It should be noted that inclusion of a tobacco material into the compositions and products described herein is meant to be optional and is not required. In some embodiments, oral products as described herein can generally be characterized as being tobacco free-alternatives. For example, in some embodiments, oral products of the present disclosure may be said to be completely free or substantially free of tobacco material (other than purified natural or synthetic nicotine as an active ingredient). Oral products that are referred to as "completely free of" or "substantially free of" a tobacco material herein are meant to refer to oral products that can be characterized as having less than about 1.0% by weight, less than about 0.5% by weight, less than about 0.1% by weight of tobacco material, or 0% by weight of tobacco material.

Ion Pairing

In certain embodiments, the material or composition within the oral pouched products disclosed herein may combine a basic amine and a non-polar or lipophilic organic acid salt in an acidic matrix which exhibit enhanced retention of the initial basic amine content during storage, and are predicted to deliver more of the basic amine to the user upon use of the composition, relative to a composition which contains a polar organic acid salt in an acidic matrix (e.g., citric acid or sodium citrate). Surprisingly, according to the present disclosure, it has been found that in certain embodiments, the presence of a non-polar or lipophilic organic acid salt enhanced composition stability and enhanced membrane permeability of the nicotine in a model system of oral absorption at an acidic pH, relative to a composition configured for oral use which included a polar organic acid salt. The enhanced nicotine permeation is particularly surprising in view of the predicted decrease in permeability associated with nicotine protonation under acidic conditions.

For customer satisfaction, it is desirable to provide a basic amine-containing oral product configured for oral use which retains the initial basic amine content during storage, and which delivers substantially the full amount of basic amine initially present in the oral product. Embodiments of the products disclosed herein can comprise at least one filler; a basic amine, such as nicotine or a nicotine component; water; and an organic acid, an alkali metal salt of an organic acid, or a combination thereof, wherein the organic acid has a log P value of from about 1.4 to about 8.0. At least a portion of the basic amine is associated with at least a portion of the organic acid or the alkali metal salt thereof. The association is in the form of a basic amine-organic acid salt, an ion pair between the basic amine and a conjugate base of the organic acid, or both. The relative amounts of the various components within the oral product composition may vary, and typically are selected so as to provide the desired sensory and performance characteristics to the oral product. The example individual components of the composition are described further herein below.

As disclosed herein, at least a portion of the basic amine is associated with at least a portion of the organic acid or the alkali metal salt thereof. Depending on multiple variables (concentration, pH, nature of the organic acid, and the like), the basic amine present in the composition can exist in multiple forms, including ion paired, in solution (i.e., fully solvated), as the free base, as a cation, as a salt, or any combination thereof. In some embodiments, the association between the basic amine and at least a portion of the organic acid or the alkali metal salt thereof is in the form of an ion pair between the basic amine and a conjugate base of the organic acid.

Ion pairing describes the partial association of oppositely charged ions in relatively concentrated solutions to form distinct chemical species called ion pairs. The strength of the association (i.e., the ion pairing) depends on the electrostatic force of attraction between the positive and negative ions (i.e., a protonated basic amine such as nicotine, and the conjugate base of the organic acid). By "conjugate base" is meant the base resulting from deprotonation of the corresponding acid (e.g., benzoate is the conjugate base of benzoic acid). On average, a certain population of these ion pairs exists at any given time, although the formation and dissociation of ion pairs is continuous. In the oral products and compositions disclosed herein, and/or upon oral use of said products and compositions (e.g., upon contact with saliva), the basic amine, for example nicotine, and the conjugate base of the organic acid exist at least partially in the form of an ion pair. Without wishing to be bound by theory, it is believed that such ion pairing may minimize chemical degradation of the basic amine and/or enhance the oral availability of the basic amine (e.g., nicotine). At alkaline pH values (e.g., such as from about 7.5 to about 9), certain basic amines, for example nicotine, are largely present in the free base form, which has relatively low water solubility, and low stability with respect to evaporation and oxidative decomposition, but high mucosal availability. Conversely, at acidic pH values (such as from about 6.5 to about 4), certain basic amines, for example nicotine, are largely present in a protonated form, which has relatively high water solubility, and higher stability with respect to evaporation and oxidative decomposition, but low mucosal availability. Surprisingly, according to the present disclosure, it has been found that the properties of stability, solubility, and availability of the nicotine in a composition configured for oral use can be mutually enhanced through ion pairing or salt formation of nicotine with appropriate organic acids and/or their conjugate bases. Specifically, nicotine-organic acid ion pairs of moderate lipophilicity result in favorable stability and absorption properties. Lipophilicity is conveniently measured in terms of log P, the partition coefficient of a molecule between a lipophilic phase and an aqueous phase, usually octanol and water, respectively. An octanol-water partitioning favoring distribution of a basic amine-organic acid ion pair into octanol is predictive of good absorption of the basic amine present in the composition through the oral mucosa.

As noted above, at alkaline pH values (e.g., such as from about 7.5 to about 9), nicotine is largely present in the free base form (and accordingly, a high partitioning into octanol), while at acidic pH values (such as from about 6.5 to about 4), nicotine is largely present in a protonated form (and accordingly, a low partitioning into octanol). Surprisingly, according to the present disclosure, it has been found that an ion pair between certain organic acids (e.g., having a log P value of from about 1.4 to about 8.0. such as from about 1.4 to about 4.5, allows nicotine partitioning into octanol consistent with that predicted for nicotine partitioning into octanol at a pH of 8.4.

One of skill in the art will recognize that the extent of ion pairing in the disclosed oral products, both before and during use by the consumer, may vary based on, for example, pH, the nature of the organic acid, the concentration of basic amine, the concentration of the organic acid or conjugate base of the organic acid present in the composition, the moisture content of the composition, the ionic strength of the composition, and the like. One of skill in the art will also recognize that ion pairing is an equilibrium process influenced by the foregoing variables. Accordingly, quantification of the extent of ion pairing is difficult or impossible by calculation or direct observation. However, as disclosed herein, the presence of ion pairing may be demonstrated through surrogate measures such as partitioning of the basic amine between octanol and water or membrane permeation of aqueous solutions of the basic amine plus organic acids and/or their conjugate bases.

Organic Acid

In some embodiments, the material or composition may comprise at least one organic acid, an alkali metal salt of an organic acid, or a combination thereof. As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($-CO_2H$) or sulfonic acids ($-SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient, such as a tobacco material).

Suitable organic acids will typically have a range of lipophilicities (i.e., a polarity giving an appropriate balance of water and organic solubility). Typically, lipophilicities of suitable organic acids, as indicated by log P, will vary between about 1 and about 12 (more soluble in octanol than in water). In some embodiments, the organic acid has a log P value of from about 3 to about 12, e.g., from about 3.0, about 3.5, about 4.0, about 4.5, about 5.0, about 5.5, about 6.0, about 6.5, about 7.0, about 7.5, or about 8.0, to about 8.5, about 9.0, about 9.5, about 10.0, about 10.5, about 11.0, about 11.5, or about 12.0. In certain embodiments, lipophilicities of suitable organic acids, as indicated by log P, will vary between about 1.4 and about 4.5 (more soluble in octanol than in water). In some embodiments, the organic acid has a log P value of from about 1.5 to about 4.0, e.g., from about 1.5, about 2.0, about 2.5, or about 3.0, to about 3.5, about 4.0, about 4.5, or about 5.0. Particularly suitable organic acids have a log P value of from about 1.7 to about 4, such as from about 2.0, about 2.5, or about 3.0, to about 3.5, or about 4.0. In specific embodiments, the organic acid has a log P value of about 2.5 to about 3.5. In some embodiments, organic acids outside this range may also be utilized for various purposes and in various amounts, as described further herein below. For example, in some embodiments, the organic acid may have a log P value of greater than about 4.5, such as from about 4.5 to about 12.0. Particularly, the presence of certain solvents or solubilizing agents (e.g., inclusion in the composition of glycerin or propylene glycol) may extend the range of lipophilicity (i.e., values of log P higher than 4.5, such as from about 4.5 to about 12.0).

Without wishing to be bound by theory, it is believed that moderately lipophilic organic acids (e.g., log P of from about 1.4 to about 4.5) produce ion pairs with nicotine which are of a polarity providing good octanol-water partitioning of the ion pair, and hence partitioning of nicotine, into octanol versus water. As discussed above, such partitioning into octanol is predictive of favorable oral availability.

In some embodiments, the organic acid is a carboxylic acid or a sulfonic acid. The carboxylic acid or sulfonic acid functional group may be attached to any alkyl, cycloalkyl, heterocycloalkyl, aryl, or heteroaryl group having, for example, from one to twenty carbon atoms ($C_1$-$C_{20}$). In some embodiments, the organic acid is an alkyl, cycloalkyl, heterocycloalkyl, aryl, or heteroaryl carboxylic or sulfonic acid.

As used herein, "alkyl" refers to any straight chain or branched chain hydrocarbon. The alkyl group may be saturated (i.e., having all spa carbon atoms), or may be unsaturated (i.e., having at least one site of unsaturation). As used herein, the term "unsaturated" refers to the presence of a carbon-carbon, $sp^2$ double bond in one or more positions within the alkyl group. Unsaturated alkyl groups may be mono- or polyunsaturated. Representative straight chain alkyl groups include, but are not limited to, methyl, ethyl, n-propyl, n-butyl, n-pentyl, and n-hexyl. Branched chain alkyl groups include, but are not limited to, isopropyl, sec-butyl, isobutyl, tert-butyl, isopentyl, and 2-methylbutyl. Representative unsaturated alkyl groups include, but are not limited to, ethylene or vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An alkyl group can be unsubstituted or substituted.

"Cycloalkyl" as used herein refers to a carbocyclic group, which may be mono- or bicyclic. Cycloalkyl groups include rings having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted, and may include one or more sites of unsaturation (e.g., cyclopentenyl or cyclohexenyl).

The term "aryl" as used herein refers to a carbocyclic aromatic group. Examples of aryl groups include, but are not limited to, phenyl and naphthyl. An aryl group can be unsubstituted or substituted.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl group comprises up to 20 carbon atoms and from 1 to 3 heteroatoms selected from N, O, and S. A heteroaryl or heterocycloalkyl may be a monocycle having 3 to 7 ring members (for example, 2 to 6 carbon atoms and 1 to 3 heteroatoms selected from N, O, and S) or a bicycle having 7 to 10 ring members (for example, 4 to 9 carbon atoms and 1 to 3 heteroatoms selected from N, O, and S), for example: a bicyclo[4,5], [5,5], [5,6], or [6,6] system. Examples of heteroaryl groups include by way of example and not limitation, pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl. Examples of heterocycloalkyls include by way of example and not limitation, dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl. Heteroaryl and heterocycloalkyl groups can be unsubstituted or substituted.

"Substituted" as used herein and as applied to any of the above alkyl, aryl, cycloalkyl, heteroaryl, heterocyclyl, means that one or more hydrogen atoms are each independently replaced with a substituent. Typical substituents include, but are not limited to, —Cl, Br, F, alkyl, —OH, —$OCH_3$, $NH_2$, —$NHCH_3$, —$N(CH_3)_2$, —CN, —NC(=O)$CH_3$, —C(=O)—, —C(=O)$NH_2$, and —C(=O)$N(CH_3)_2$. Wherever a group is described as "optionally substituted," that group can be substituted with one or more of the above substituents, independently selected for each occasion. In some embodiments, the substituent may be one or more methyl groups or one or more hydroxyl groups.

In some embodiments, the organic acid is an alkyl carboxylic acid. Non-limiting examples of alkyl carboxylic acids include formic acid, acetic acid, propionic acid, butyric acid, valeric acid, caproic acid, heptanoic acid, octanoic acid, nonanoic acid, decanoic acid, undecanoic acid, dodecanoic acid, stearic acid, oleic acid, linoleic acid, linolenic acid, and the like.

In some embodiments, the organic acid is an alkyl sulfonic acid. Non-limiting examples of alkyl sulfonic acids include propanesulfonic acid, heptanesulfonic acid, and octanesulfonic acid.

In some embodiments, the alkyl carboxylic or sulfonic acid is substituted with one or more hydroxyl groups. Non-limiting examples include glycolic acid, 4-hydroxybutyric acid, and lactic acid.

In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like.

In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid.

Further non-limiting examples of organic acids which may be useful in certain embodiments include 2-(4-isobutylphenyl)propanoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid (L), aspartic acid (L), alpha-methylbutyric acid, camphoric acid (+), camphor-10-sulfonic acid (+), cinnamic acid, cyclamic acid, dodecylsulfuric acid, ethane-1,2-disulfonic acid, ethanesulfonic acid, furoic acid, galactaric acid, gentisic acid, glucoheptonic acid, gluconic acid, glucuronic acid, glutamic acid, glycerophosphoric acid, glycolic acid, hippuric acid, isobutyric acid, isovaleric acid, lactobionic acid, lauric acid, levulinic acid, malic acid, malonic acid, mandelic acid, methanesulfonic acid, naphthalene-1,5-disulfonic acid, naphthalene-2-sulfonic acid, oleic acid, palmitic acid, pamoic acid, phenylacetic acid, pyroglutamic acid, pyruvic acid, sebacic acid, stearic acid, and undecylenic acid.

Examples of suitable acids include, but are not limited to, the list of organic acids in Table 1.

TABLE 1

Non-limiting examples of suitable organic acids

| Acid Name | log(P) |
|---|---|
| benzoic acid | 1.9 |
| phenylacetic | 1.4 |
| p-toluic acid | 2.3 |
| ethyl benzoic acid | 2.9 |
| isopropyl benzoic acid | 3.5 |
| 4-phenylbutyric | 2.4 |
| 2-napthoxyacetic acid | 2.5 |
| napthylacetic acid | 2.7 |
| heptanoic acid | 2.5 |
| octanoic acid | 3.05 |
| nonanoic acid | 3.5 |
| decanoic acid | 4.09 |
| 9-deceneoic acid | 3.3 |
| 2-deceneoic acid | 3.8 |
| 10-undecenoic acid | 3.9 |
| dodecandioic acid | 3.2 |
| dodecanoic acid | 4.6 |
| myristic acid | 5.3 |
| palmitic acid | 6.4 |
| stearic acid | 7.6 |
| cyclohexanebutanoic acid | 3.4 |
| 1-heptanesulfonic acid | 2.0 |
| 1-octanesulfonic acid | 2.5 |
| 1-nonanesulfonic acid | 3.1 |
| monooctyl succinate | 2.8 |
| tocopherol succinate | 10.2 |
| monomenthyl succinate | 3 |
| monomenthyl glutarate | 3.4 |
| norbixin ((2E,4E,6E,8E,10E,12E,14E,16E,18E)-4,8,13,17-tetramethylicosa-2,4,6,8,10,12,14,16,18-nonaenedioic acid) | 7.2 |

TABLE 1-continued

| Non-limiting examples of suitable organic acids | |
|---|---|
| Acid Name | log(P) |
| bixin ((2E,4E,6E,8E,10E,12E,14E,16Z,18E)-20-methoxy-4,8,13,17-tetramethyl-20-oxoicosa-2,4,6,8,10,12,14,16,18-nonaenoic acid) | 7.5 |

In some embodiments, the organic acid is benzoic acid, a toluic acid, benzenesulfonic acid, toluenesulfonic acid, hexanoic acid, heptanoic acid, decanoic acid, or octanoic acid. In some embodiments, the organic acid is benzoic acid, octanoic acid, or decanoic acid. In some embodiments, the organic acid is octanoic acid. In some embodiments, the organic acid is benzoic acid.

In some embodiments, the organic acid is a mono ester of a di- or poly-acid, such as mono-octyl succinate, mono-octyl fumarate, or the like. For example, the organic acid is a mono ester of a dicarboxylic acid or a poly-carboxylic acid. In some embodiments, the dicarboxylic acid is malonic acid, succinic acid, glutaric acid, adipic acid, fumaric acid, maleic acid, or a combination thereof. In some embodiments, the dicarboxylic acid is succinic acid, glutaric acid, fumaric acid, maleic acid, or a combination thereof. In some embodiments, the dicarboxylic acid is succinic acid, glutaric acid, or a combination thereof.

In some embodiments, the alcohol forming the mono ester of the dicarboxylic acid is a lipophilic alcohol. Examples of suitable lipophilic alcohols include, but are not limited to, octanol, menthol, and tocopherol. In some embodiments, the organic acid is an octyl mono ester of a dicarboxylic acid, such as monooctyl succinate, monooctyl fumarate, or the like. In some embodiments, the organic acid is a monomenthyl ester of a dicarboxylic acid. Certain menthyl esters may be desirable in oral compositions as described herein by virtue of the cooling sensation they may provide upon use of the product comprising the composition. In some embodiments, the organic acid is monomenthyl succinate, monomenthyl fumarate, monomenthyl glutarate, or a combination thereof. In some embodiments, the organic acid is a monotocopheryl ester of a dicarboxylic acid. Certain tocopheryl esters may be desirable in oral compositions as described herein by virtue of the antioxidant effects they may provide. In some embodiments, the organic acid is tocopheryl succinate, tocopheryl fumarate, tocopheryl glutarate, or a combination thereof.

In some embodiments, the organic acid is a carotenoid derivative having one or more carboxylic acids. Carotenoids are tetraterpenes, meaning that they are produced from 8 isoprene molecules and contain 40 carbon atoms. Accordingly, they are usually lipophilic due to the presence of long unsaturated aliphatic chains, and are generally yellow, orange, or red in color. Certain carotenoid derivatives can be advantageous in oral compositions by virtue of providing both ion pairing and serving as a colorant in the composition. In some embodiments, the organic acid is 2E,4E,6E,8E,10E,12E,14E,16Z,18E)-20-methoxy-4,8,13,17-tetramethyl-20-oxoicosa-2,4,6,8,10,12,14,16,18-nonaenoic acid (bixin) or an isomer thereof. Bixin is an apocarotenoid found in annatto seeds from the achiote tree (*Bixa orellana*), and is the naturally occurring pigment providing the reddish orange color to annatto. Bixin is soluble in fats and alcohols but insoluble in water, and is chemically unstable when isolated, converting via isomerization into the double bond isomer, trans-bixin (β-bixin), having the structure:

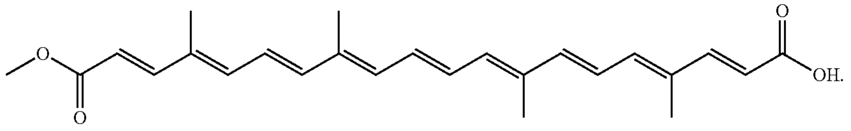 [SMILES: COC(=O)/C=C/C(C)=C/C=C/C(C)=C/C=C/C=C(C)/C=C/C=C(C)/C=C/C(=O)O]

In some embodiments, the organic acid is (2E,4E,6E,8E,10E,12E,14E,16E,18E)-4,8,13,17-tetramethylicosa-2,4,6,8,10,12,14,16,18-nonaenedioic acid (norbixin), a water soluble hydrolysis product of bixin having the structure:

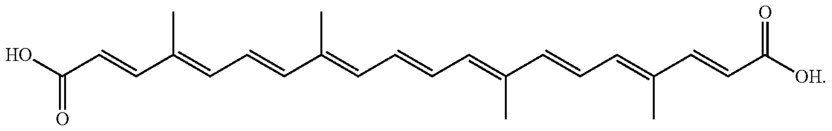 [SMILES: CC(/C=C/C=C(C)/C=C/C(=O)O)=C\C=C\C=C(C)\C=C\C=C(C)\C=C\C(=O)O]

The selection of organic acid may further depend on additional properties in addition to or without consideration to the log P value. For example, an organic acid should be one recognized as safe for human consumption, and which has acceptable flavor, odor, volatility, stability, and the like. Determination of appropriate organic acids is within the purview of one of skill in the art.

In some embodiments, more than one organic acid may be present. For example, the composition may comprise two, or three, or four, or more organic acids. Accordingly, reference herein to “an organic acid” contemplates mixtures of two or more organic acids. The relative amounts of the multiple organic acids may vary. For example, a composition may comprise equal amounts of two, or three, or more organic acids, or may comprise different relative amounts. In this manner, it is possible to include certain organic acids (e.g., citric acid or myristic acid) which have a log P value outside the desired range, when combined with other organic acids to provide the desired average log P range for the combination. In some embodiments, it may be desirable to include organic acids in the composition which have log P values outside the desired range for purposes such as, but not limited to, providing desirable organoleptic properties, stability, as flavor components, and the like. Further, certain lipophilic organic acids have undesirable flavor and or aroma characteristics which would preclude their presence as the sole organic acid (e.g., in equimolar or greater quantities relative to nicotine). Without wishing to be bound by theory, it is believed that a combination of different organic acids may provide the desired ion pairing while the concentration of any single organic acid in the composition remains below the threshold which would be found objectionable from a sensory perspective.

For example, in some embodiments, the organic acid may comprise from about 1 to about 5 or more molar equivalents of benzoic acid relative to nicotine, combined with e.g., about 0.2 molar equivalents of octanoic acid or a salt thereof, and 0.2 molar equivalents of decanoic acid or a salt thereof.

In some embodiments, the organic acid is a combination of any two organic acids selected from the group consisting of benzoic acid, a toluic acid, benzenesulfonic acid, toluenesulfonic acid, hexanoic acid, heptanoic acid, decanoic acid, and octanoic acid. In some embodiments, the organic acid is a combination of benzoic acid, octanoic acid, and decanoic acid, or benzoic and octanoic acid. In some embodiments, the composition comprises citric acid in addition to one or more of benzoic acid, a toluic acid, benzenesulfonic acid, toluenesulfonic acid, hexanoic acid, heptanoic acid, decanoic acid, and octanoic acid.

In some embodiments, the composition comprises an alkali metal salt of an organic acid. For example, at least a portion of the organic acid may be present in the composition in the form of an alkali metal salt. Suitable alkali metal salts include lithium, sodium, and potassium. In some embodiments, the alkali metal is sodium or potassium. In some embodiments, the alkali metal is sodium. In some embodiments, the composition comprises an organic acid and a sodium salt of the organic acid.

In some embodiments, the composition comprises benzoic acid and sodium benzoate, octanoic acid and sodium octanoate, decanoic acid and sodium decanoate, or a combination thereof.

In some embodiments, the ratio of the organic acid to the sodium salt of the organic acid is from about 0.1 to about 10, such as from about 0.1, about 0.25, about 0.3, about 0.5, about 0.75, or about 1, to about 2, about 5, or about 10. For example, in some embodiments, both an organic acid and the sodium salt thereof are added to the other components of the composition, wherein the organic acid is added in excess of the sodium salt, in equimolar quantities with the sodium salt, or as a fraction of the sodium salt. One of skill in the art will recognize that the relative amounts will be determined by the desired pH of the composition, as well as the desired ionic strength. For example, the organic acid may be added in a quantity to provide a desired pH level of the composition, while the alkali metal (e.g., sodium) salt is added in a quantity to provide the desired extent of ion pairing. As one of skill in the art will understand, the quantity of organic acid (i.e., the protonated form) present in the composition, relative to the alkali metal salt or conjugate base form present in the composition, will vary according to the pH of the composition and the pKa of the organic acid, as well as according to the actual relative quantities initially added to the composition.

The amount of organic acid and/or an alkali metal salt thereof present in the composition, relative to nicotine, may vary. Generally, as the concentration of the organic acid (or the conjugate base thereof) increases, the percent of nicotine that is ion paired with the organic acid increases. This typically increases the partitioning of the nicotine, in the form of an ion pair, into octanol versus water as measured by the log P (the $\log_{10}$ of the partitioning coefficient). In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the nicotine component, calculated as free base nicotine.

In some embodiments, the composition comprises from about 2 to about 10, or from about 2 to about 5 molar equivalents of the organic acid, the alkali metal salt thereof, or the combination thereof, to nicotine, on a free-base nicotine basis. In some embodiments, the organic acid, the alkali metal salt thereof, or the combination thereof, is present in a molar ratio with the nicotine from about 2, about 3, about 4, or about 5, to about 6, about 7, about 8, about 9, or about 10. In embodiments wherein more than one organic acid, alkali metal salt thereof, or both, are present, it is to be understood that such molar ratios reflect the totality of the organic acids present.

In certain embodiments the organic acid inclusion is sufficient to provide a composition pH of from about 4.0 to about 9.0, such as from about 4.5 to about 7.0, or from about 5.5 to about 7.0, from about 4.0 to about 5.5, or from about 7.0 to about 9.0. In some embodiments, the organic acid inclusion is sufficient to provide a composition pH of from about 4.5 to about 6.5, for example, from about 4.5, about 5.0, or about 5.5, to about 6.0, or about 6.5. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5. In other embodiments, a mineral acid (e.g., hydrochloric acid, sulfuric acid, phosphoric acid, or the like) is added to adjust the pH of the composition to the desired value.

In some embodiments, the organic acid is added as the free acid, either neat (i.e., native solid or liquid form) or as a solution in, e.g., water, to the other composition components. In some embodiments, the alkali metal salt of the organic acid is added, either neat or as a solution in, e.g., water, to the other composition components. In some embodiments, the organic acid and the basic amine (e.g., nicotine) are combined to form a salt, either before addition to the composition, or the salt is formed within and is present in the composition as such. In other embodiments, the organic acid and basic amine (e.g., nicotine) are present as individual components in the composition, and form an ion pair upon contact with moisture (e.g., saliva in the mouth of the consumer).

In some embodiments, the composition comprises nicotine benzoate and sodium benzoate (or other alkali metal benzoate). In other embodiments, the composition comprises nicotine and an organic acid, wherein the organic acid is a monoester of a dicarboxylic acid or is a carotenoid derivative having one or more carboxylic acids.

In some embodiments, the composition further comprises a solubility enhancer to increase the solubility of one or more of the organic acid or salt thereof. Suitable solubility enhancers include, but are not limited to, humectants as described herein such as glycerol or propylene glycol.

Basic Amine

In one or more embodiments, the material or composition may comprise a basic amine. By "basic amine" is meant a molecule including at least one basic amine functional group. Examples of basic amines include, but are not limited to, alkaloids. By "basic amine functional group" is meant a group containing a nitrogen atom having a lone pair of electrons. The basic amine functional group is attached to or incorporated within the molecule through one or more covalent bonds to the said nitrogen atom. The basic amine may be a primary, secondary, or tertiary amine, meaning the nitrogen bears one, two, or three covalent bonds to carbon atoms. By virtue of the lone pair of electrons on the nitrogen atom, such amines are termed "basic", meaning the lone electron pair is available for hydrogen bonding. The basicity (i.e., the electron density on the nitrogen atom and consequently the availability and strength of hydrogen bonding to the nitrogen atom) of the basic amine may be influenced by the nature of neighboring atoms, the steric bulk of the molecule, and the like.

Generally, the basic amine is released from the composition and absorbed through the oral mucosa, thereby entering the blood stream, where it is circulated systemically. Generally, the basic amine is present in or as an active ingredient in the composition, as described herein below. In some embodiments, the basic amine is nicotine or a nicotine component. By "nicotine component" is meant any suitable form of nicotine as discussed herein (e.g., free base, salt, or ion pair) for providing oral absorption of at least a portion of the nicotine present. In some embodiments, suitable forms of nicotine may include naturally-occurring and/or synthetic nicotine. Nicotine is released from the composition and absorbed through the oral mucosa, thereby entering the blood stream, where it is circulated systemically.

Typically, the nicotine component is selected from the group consisting of nicotine free base, nicotine as an ion pair, and a nicotine salt. In some embodiments, at least a portion of the nicotine is in its free base form. In some embodiments, at least a portion of the nicotine is present as a nicotine salt, or at least a portion of the nicotine is present as an ion pair with at least a portion of the organic acid or the conjugate base thereof, as disclosed herein above.

Typically, the nicotine component (calculated as the free base) is present in a concentration of at least about 0.001% by weight of the composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the composition.

Further Additives

In some embodiments, one or more further additives can be included in the material. For example, the compositions can be processed, blended, formulated, combined and/or mixed with other materials or ingredients. The additives can be artificial, or can be obtained or derived from herbal or biological sources. Specific types of further additives that may be included are further described below.

Water

In some embodiments, the material may include a content of water. The water content of the composition within the product, prior to use by a consumer of the product, may vary according to the desired properties. Typically, the composition, as present within the product prior to insertion into the mouth of the user, can comprise less than 60%, less than 50%, less than 40%, less than 30%, less than 20%, less than 10%, or less than 5% by weight of water. For example, total water content in the composition and/or product may be in the range of about 0.1% to about 60%, about 1% to about 50%, about 1.5% to about 40%, or about 2% to about 25% by weight of water. In some embodiments, the compositions and products may include at least 1%, at least 2%, at least 5%, at least 10%, or at least 20% by weight water.

Salts

In some embodiments, the material may further comprise a salt (e.g., alkali metal salts), typically employed in an amount sufficient to provide desired sensory attributes to the compositions and products. Non-limiting examples of suitable salts include sodium chloride, potassium chloride, ammonium chloride, flour salt, and the like. When present, a representative amount of salt is about 0.5 percent by weight or more, about 1.0 percent by weight or more, or at about 1.5 percent by weight or more, but will typically make up about 10 percent or less of the total weight of the composition or product, or about 7.5 percent or less or about 5 percent or less (e.g., about 0.5 to about 5 percent by weight).

Sweeteners

The material also may include one or more sweeteners. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, isomaltulose, stevia, honey, and the like. Examples of artificial sweeteners include sucralose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 20 percent or more of the of the composition by weight, for example, from about 0.1 to about 1%, from about 1 to about 5%, from about 5 to about 10%, or from about 10 to about 20% of the material on a weight basis, based on the total weight of the material.

Binding Agents

In some embodiments, the material may include one or more binding agents. A binder (or combination of binders) may be employed in certain embodiments, in amounts sufficient to provide the desired physical attributes and physical integrity to the composition, and binders also often function as thickening or gelling agents. Typical binders can be organic or inorganic, or a combination thereof. Representative binders include povidone, sodium alginate, starch-based binders, pectin, carrageenan, pullulan, zein, and the like, and combinations thereof. In some embodiments, the binder comprises pectin or carrageenan or combinations thereof. The amount of binder utilized can vary, but is typically up to about 30 weight percent, and certain embodiments are characterized by a binder content of at least about 0.1% by weight, such as about 1 to about 30% by weight, or about 5 to about 10% by weight, based on the total weight of the material.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the material.

Humectants

In certain embodiments, one or more humectants may be employed in the mixture. Examples of humectants include, but are not limited to, glycerin, propylene glycol, and the like. Where included, the humectant is typically provided in an amount sufficient to provide desired moisture attributes to the compositions. Further, in some instances, the humectant may impart desirable flow characteristics to the composition for depositing in a mold. When present, a humectant will typically make up about 5% or less of the weight of the material (e.g., from about 0.5 to about 5% by weight). When present, a representative amount of humectant is about 0.1% to about 1% by weight, or about 1% to about 5% by weight, based on the total weight of the material.

pH Adjusters/Buffering Agents

In certain embodiments, the materials of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Where present, the buffering agent is typically present in an amount less than about 5 percent based on the weight of the material, for example, from about 0.5% to about 5%, such as, e.g., from about 0.75% to about 4%, from about 0.75% to about 3%, or from about 1% to about 2% by weight, based on the total weight of the material. Non-limiting examples of suitable buffers include alkali metals acetates, glycinates, phosphates, glycerophosphates, citrates, carbonates, hydrogen carbonates, borates, or mixtures thereof.

Colorants

In some embodiments, the material may include one or more colorants. A colorant may be employed in amounts sufficient to provide the desired physical attributes to the composition or product. Examples of colorants include various dyes and pigments, such as caramel coloring and titanium dioxide. The amount of colorant utilized in the compositions or products can vary, but when present is typically up to about 3 weight percent, such as from about 0.1%, about 0.5%, or about 1%, to about 3% by weight, based on the total weight of the material.

Examples of even further types of additives that may be used in the present materials include thickening or gelling agents (e.g., fish gelatin), emulsifiers, oral care additives (e.g., thyme oil, *eucalyptus* oil, and zinc), preservatives (e.g., potassium sorbate and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final mixture, with an example range of up to about 10% by weight, based on total weight of the material (e.g., about 0.1 to about 5% by weight).

The aforementioned additives can be employed together (e.g., as additive formulations) or separately (e.g., individual additive components can be added at different stages involved in the preparation of the final material). Furthermore, the aforementioned types of additives may be encapsulated as provided in the final product or material to be included within the final product. Example encapsulated additives are described, for example, in WO2010/132444 to Atchley, which has been previously incorporated by reference herein.

Particles

In some embodiments, any one or more of a filler, a tobacco material, and the overall material described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, typically in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, such as 300 μm.

In some embodiments, any particulate material referenced herein (e.g., filler component, tobacco material, and the overall material) can be characterized as having at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 90% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 99% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 μm to about 1000 μm, such as from about 0.05 μm to about 750 μm, such as from about 0.1 μm to about 500 μm, such as from about 0.25 μm to about 500 μm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 μm to about 400 μm, such as from about 50 μm to about 350 μm, such as from about 100 μm to about 350 μm, such as from about 200 μm to about 300 μm.

Preparation of the Material for Inclusion within the Pouch

The manner by which the various components of the material are combined may vary. As such, the overall mixture of various components with e.g., powdered mixture components may be relatively uniform in nature. The components noted above, which may be in liquid or dry solid form, can be admixed in a pretreatment step prior to mixture with any remaining components of the material, or simply mixed together with all other liquid or dry ingredients. The various components of the material may be contacted, combined, or mixed together using any mixing technique or equipment known in the art. Any mixing method that brings the ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the material are prepared such that the mixture thereof may be used in a starch molding process for forming the mixture. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

The amount of material contained within each product unit, for example, a pouch, may vary. In some embodiments, the weight of the mixture within each pouch is at least about 50 mg, for example, from about 50 mg to about 2 grams, from about 100 mg to about 1.5 grams, or from about 200 to about 700 mg. In some smaller embodiments, the weight of the mixture within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

Methods of Manufacturing Multi-Compartment Oral Pouched Products

Some aspects of the present disclosure provide methods of manufacturing multi-compartment oral pouch products. For example, such methods may include positioning a first composition adapted for oral use and a second composition adapted for oral use between a bottom layer of fleece material and a top layer of fleece material. Typically, the first composition is spaced apart from the second composition a defined distance to prevent contact between the first composition and the second composition. After positioning the compositions between the layers of fleece material, a portion of the top layer of fleece material and a portion of the bottom layer of fleece material are sealed proximate to the defined distance between the first composition and the second composition to provide an interior seam at least partially separating the first composition from the second composition. As noted herein above, the sealed seam may be provided in the form of a fully welded seam (e.g., using conventional heat sealing techniques, for example) or the sealed seam may be provided in the form of a partially sealed seam (e.g., using conventional perforation methods, for example). Heat sealing can be accomplished using direct application of heat or by other means, such as ultrasonic sealing, vacuum sealing, and the like. In certain embodiments, a perforated or partially sealed seam can be formed by applying an intermittent heat seal such that gaps remain in the seam where no welding occurs. Generally, the method of sealing the interior seam may vary and it is understood that any sealing method commonly known in the art for sealing fleece materials and/or water-dispersible film materials would be suitable. Although fleece materials are discussed herein by way of example, as noted above, pouch materials according to the present disclosure are not limited to fleece materials and it should be understood that the methods as described herein are likewise applicable to other pouch material (e.g., such as pouch materials formed of a water dispersible film material and the like). After sealing the interior seam, a perimeter of the top layer of fleece material and the bottom layer of fleece material are sealed forming the multi-compartment oral pouch.

As noted above, in some embodiments of methods, the interior seam can be a fully welded seam that completely separates the first composition from the second composition. In other embodiments, the interior seam can be a perforated seam that partially separates the first composition and the second composition. In some embodiments, the first composition can be different from the second composition such that the composition in the formed first compartment after sealing (i.e., the first composition) is different from the composition in the formed second compartment after sealing (i.e., the second composition). In some embodiments of methods as described herein, the first composition and the second composition may be inserted within the pouch material prior to forming the two or more compartments (as noted above) or, alternatively, the two or more compartments may be pre-formed in the pouch material and partially sealed prior to inserting the first composition and the second composition into their respective compartments. In the latter example, the partially sealed compartments may be partially sealed in a manner sufficient to receive and retain the inserted compositions prior to application of a final seal to the product.

Additional methods of manufacturing multi-compartment oral pouches are also provided in the present disclosure. In some embodiments, for example, a method of manufacturing multi-compartment oral pouches comprises positioning a first composition adapted for oral use between a bottom layer of fleece material and an intermediate layer of fleece material. Next, a second composition adapted for oral use may be positioned between the intermediate layer of fleece material and a top layer of fleece material. After the composition charges have been positioned within the layers of fleece material, a perimeter of the top layer of fleece material, the intermediate layer of fleece material, and the bottom layer of fleece material can be sealed to provide a multi-compartment oral pouch. Generally, the method of sealing the layers of fleece material may vary and, as noted herein, it is understood that any sealing method commonly known in the art for sealing fleece materials would be suitable.

Still other methods of manufacturing multi-compartment oral pouches are provided in the present disclosure. In some embodiments, for example, a first compartment of an outer water-permeable pouch may be formed and filled with a first composition as described herein above. After insertion of the first composition within the first compartment of the outer water-permeable pouch the first compartment may be sealed using any sealing technique previously described herein. Next, a second compartment of an outer water-permeable pouch (larger than the first compartment) may be formed and the first compartment of the outer water-permeable pouch is placed within an annular region within the first compartment. After insertion of the first compartment within the second compartment, the second compartment may be filled with a second composition. As described herein, the second composition may be the same or different than the first composition. After filling the second compartment with the second composition, the second compartment is then sealed using one or more sealing techniques as described herein to form a multi-compartment oral pouched product as described herein. In such embodiments, the first compartment is contained entirely within the second compartment such that the second compartment surrounds the first compartment forming a multi-compartment oral pouch.

Various manufacturing apparatuses and methods can be used to create pouched products and such manufacturing apparatuses can be used, in combination with the methods provided herein, to create multi-compartment oral pouched products as described herein. For example, US Appl. Pub. No. 2012/0055493 to Novak, III et al., incorporated by reference in its entirety, relates to an apparatus and process for providing pouch material formed into a tube for use in the manufacture of smokeless tobacco products. Similar apparatuses that incorporate equipment for supplying a continuous supply of a pouch material (e.g., a pouch processing unit adapted to supply a pouch material to a continuous tube forming unit for forming a continuous tubular member from the pouch material) can be used to create a multi-compartment pouched product described herein, wherein the pouch material is a needle-punched fleece as provided herein. Representative equipment for forming such a continuous tube of pouch material is disclosed, for example, in US Appl. Pub. No. 2010/0101588 to Boldrini et al., which is incorporated herein by reference in its entirety. The apparatus further includes equipment for supplying pouched material to the continuous tubular member such that, when the continuous tubular member is subdivided and sealed into discrete pouch portions, each pouch portion includes a charge of a composition adapted for oral use. Representative equipment for supplying the filler material is disclosed, for example, in US Pat. Appl. Pub. No. US 2010/0018539 to Brinkley, which is incorporated herein by reference in its entirety. In some instances, the apparatus may include a subdividing unit for subdividing the continuous tubular member into individual pouch portions and, once subdivided into the individual pouch portions, may also include a sealing unit for sealing one or more ends of each pouch portion. In other instances, the continuous tubular member may be sealed into individual pouch portions with a sealing unit and then, once the individual pouch portions are sealed, the continuous tubular member may be subdivided into discrete individual pouch portions by a subdividing unit, subdividing the continuous tubular member between the sealed ends of serially-disposed pouch portions. Still in other instances, sealing (closing) of the individual pouch portions of the continuous tubular member may occur substantially concurrently with the subdivision thereof, using a closing and dividing unit in combination with a typical heat sealing unit.

The amount of material contained within each multi-compartment pouch may vary. Generally, the amount of material contained within each multi-compartment pouch includes the total amount of material included in all compartments of the multi-compartment pouch. In some embodiments, the amount of material in each compartment may vary and the amount of material in each compartment may be substantially the same or different from compartment to compartment. In smaller embodiments, the dry weight of the material within each pouch is at least about 50 mg to about 150 mg. For a larger embodiment, the dry weight of the material within each pouch typically does not exceed about 300 mg to about 500 mg. In some embodiments, the dry weight of the material within each pouch is at least about 50 mg, for example, from about 50 mg to about 2 grams, from about 100 mg to about 1.5 grams, or from about 200 to about 700 mg. In some embodiments, each pouch/container may have disposed therein a flavor agent member, as described in greater detail in U.S. Pat. No. 7,861,728 to Holton, Jr. et al., which is incorporated herein by reference. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In various embodiments, the fleece materials used within the sealed pouch materials described herein can be sufficiently tacky so as to create issues with high-speed pouching equipment. Therefore, in certain embodiments, a Teflon® coating, or similar material, can be applied to one or more surfaces of the pouching equipment that touch the fleece material such as, for example, rollers, cutting instruments, and sealing devices in order to reduce and/or alleviate any problems associated with the pouch material sticking to the pouching equipment during processing.

The pouched products can further include product identifying information printed or dyed on the outer water-permeable pouch or imprinted (e.g., embossed, debossed, or otherwise pressed) on the outer water-permeable pouch, such as described in US Pat. Appl. Pub. No. 2014/0255452 to Reddick et al., which is incorporated by reference herein. As noted above, flavorants can also be incorporated into the nonwoven web if desired, such as by coating or printing an edible flavorant ink onto the nonwoven web. See, e.g., US Pat. Appl. Pub. Nos. 2012/0085360 to Kawata et al. and 2012/0103353 to Sebastian et al., each of which is herein incorporated by reference.

Products of the present disclosure configured for oral use may be packaged and stored in any suitable packaging in much the same manner that conventional types of smokeless tobacco products are packaged and stored. For example, a plurality of packets or pouches may be contained in a cylindrical container. The storage period of the product after preparation may vary. As used herein, "storage period" refers to the period of time after the preparation of the disclosed product. In some embodiments, one or more of the characteristics of the products disclosed herein (e.g., retention of whiteness, lack of color change, retention of volatile flavor components) is exhibited over some or all of the storage period. In some embodiments, the storage period (i.e., the time period after preparation) is at least one day. In some embodiments, the storage period is from about about 1 day, about 2 days, or about 3 days, to about 1 week, or from about 1 week to about 2 weeks, from about 2 weeks to about 1 month, from about 1 month to about 2 months, from about 2 months to about 3 months, from about 3 months to about 4 months, or from about 4 months to about 5 months. In some embodiments, the storage period is any number of days between about 1 and about 150. In certain embodiments, the storage period may be longer than 5 months, for example, about 6 months, about 7 months, about 8 months, about 9 months, about 10 months, about 11 months, or about 12 months.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An oral pouched product, comprising an outer water-permeable pouch having two or more compartments including a first compartment and a second compartment, each of said first and second compartments containing a composition comprising a water-soluble component capable of release through the outer water-permeable pouch, wherein the second compartment is contained entirely within the first compartment such that the first compartment surrounds the second compartment, wherein the outer water-permeable pouch comprises one or more of a fleece material and a water-dispersible film material, wherein the first compartment and the second compartment are separated by a fully or partially sealed seam in the outer-water-permeable pouch material.

2. The oral pouched product of claim 1, wherein the first compartment and the second compartment are separated by a wall structure, the wall structure providing either a non-porous barrier that prevents inter-compartment transfer of the composition contained within each compartment or a porous barrier that allows inter-compartment transfer of the composition contained within each compartment.

3. The oral pouched product of claim 2, wherein the wall structure is in the form of a fully or partially welded seam in the outer water permeable pouch.

4. The oral pouched product of claim 3, wherein the partially welded seam is in the form of a perforated seam.

5. The oral pouched product of claim 2, wherein the wall structure is a water-permeable barrier contained within the outer water-permeable pouch.

6. The oral pouched product of claim 2, further comprising a sealed outer perimeter adjacent to the first compartment, wherein at least a portion of the wall structure is in spaced relation to the sealed outer perimeter.

7. The oral pouched product of claim 6, wherein the wall structure forms a lateral perimeter surrounding a periphery of the second compartment such that the entirety of the wall structure is in spaced relation to the sealed outer perimeter.

8. The oral pouched product of claim 1, wherein the composition within each of the first and second compartments is different such that the composition within each compartment provides a different functional or sensory experience.

9. The oral pouched product of claim 8, wherein the composition within the first compartment and the composition within the second compartment comprise a different flavoring agent, a different active ingredient, or both a different flavoring agent and a different active ingredient.

10. The oral pouched product of claim 1, wherein the composition in the first compartment and the composition in the second compartment each comprise an active ingredient selected from the group consisting of a nicotine component, botanicals, nutraceuticals, stimulants, amino acids, vitamins, cannabinoids, cannabimimetics, terpenes, and combinations thereof.

11. The oral pouched product of claim 1, wherein the composition in the first compartment and the composition in the second compartment each comprise one or more additives selected from the group consisting of a flavoring agent, a salt, a sweetener, a binding agent, water, a humectant, a buffering agent and/or a pH adjuster, a tobacco material, and combinations thereof.

12. The oral pouched product of claim 1, wherein the oral pouched product is substantially free of a tobacco material.

13. The oral pouch product of claim 1, wherein the outer water-permeable pouch comprises a first layer of fleece material and a second layer of fleece material.

14. The oral pouched product of claim 13, wherein the first layer of fleece material and the second layer of fleece material are different such that the first and second layers of fleece material provide a different functional or sensory experience.

15. The oral pouched product of claim 14, wherein the first layer of fleece material includes a different flavoring agent, a different active ingredient, or both a different flavoring agent and a different active ingredient when compared to the second layer of fleece material.

16. The oral pouched product of claim 14, wherein the first layer of fleece material exhibits one or more of a different porosity, a different permeability, and a different texture when compared to the second layer of fleece material.

17. The oral pouched product of claim 1, wherein the fleece material comprises fibers selected from the group consisting of conventional cellulosic fibers, cotton fibers, wool fibers, hemp fibers, polymer/synthetic-type fibers, and combinations thereof.

18. The oral pouched product of claim 1, wherein the water dispersible film material comprises a film forming material selected from the group consisting of film-forming polysaccharides, starches, modified starches, celluloses, modified celluloses, pullulan, pectin, alginate, gums, and combinations thereof.

19. An oral pouched product, comprising an outer water-permeable pouch having two or more compartments including a first compartment and a second compartment, each of said first and second compartments containing a composition comprising a water-soluble component capable of release through the outer water-permeable pouch, wherein the outer water-permeable pouch comprises a first layer of fleece material and a second layer of fleece material, and wherein the outer water-permeable pouch further comprises at least one intermediate layer of fleece material separating the first compartment and the second compartment, wherein the first layer of fleece material, the second layer of fleece material, and the intermediate layer of fleece material are welded together along a perimeter thereof to form a sealed outer perimeter of the oral pouched product.

* * * * *